US011213506B2

(12) United States Patent
Reddell et al.

(10) Patent No.: US 11,213,506 B2
(45) Date of Patent: Jan. 4, 2022

(54) COMBINATION THERAPY FOR THE TREATMENT OR PREVENTION OF TUMOURS

(71) Applicant: QBIOTICS PTY LTD, Taringa (AU)

(72) Inventors: Paul Warren Reddell, Yungaburra (AU); Jason Kingsley Cullen, Thornside (AU); Glen Mathew Boyle, Taringa (AU); Peter Gordon Parsons, St Lucia (AU); Victoria Anne Gordon, Yungaburra (AU)

(73) Assignee: QBIOTICS PTY LTD, Taringa (AU)

( * ) Notice: Subject to any disclaimer, the term of this patent is extended or adjusted under 35 U.S.C. 154(b) by 0 days.

(21) Appl. No.: 16/496,333

(22) PCT Filed: Mar. 23, 2018

(86) PCT No.: PCT/AU2018/050277
§ 371 (c)(1),
(2) Date: Sep. 20, 2019

(87) PCT Pub. No.: WO2018/170559
PCT Pub. Date: Sep. 27, 2018

(65) Prior Publication Data
US 2020/0030279 A1 Jan. 30, 2020

(30) Foreign Application Priority Data

Mar. 23, 2017 (AU) .................. 2017901027

(51) Int. Cl.
*A61K 31/336* (2006.01)
*A61K 39/395* (2006.01)
(Continued)

(52) U.S. Cl.
CPC .......... *A61K 31/336* (2013.01); *A61K 9/0019* (2013.01); *A61K 39/39558* (2013.01); *A61P 35/00* (2018.01)

(58) Field of Classification Search
CPC ............ A61K 31/336; A61K 39/39558; A61K 9/0019; A61P 35/00
(Continued)

(56) References Cited

U.S. PATENT DOCUMENTS

2014/0155479 A1* 6/2014 Reddell .................. A61P 31/04
514/475

FOREIGN PATENT DOCUMENTS

CN 104926758 A 9/2015
WO 2007/070985 A1 6/2007
(Continued)

OTHER PUBLICATIONS

Sharon et al, Immune checkpoints in cancer clinical trials, Chinese Journal of Cancer 2014, vol. 33, issue 9,.pp. 434-444 (Year: 2014).*
(Continued)

*Primary Examiner* — Taylor V Oh
(74) *Attorney, Agent, or Firm* — Seed IP Law Group LLP

(57) ABSTRACT

The present invention relates to a combination therapy for tumours comprising the administration of an epoxytigliane compound and an immune checkpoint inhibitor. In particular embodiments, there is a method of treating a tumour and/or treating or preventing one or more bystander tumours with the therapy. Pharmaceutical compositions and kits containing epoxytigliane compounds and immune checkpoint inhibitors are also described.

29 Claims, 17 Drawing Sheets

(51) Int. Cl.
  *A61K 9/00* (2006.01)
  *A61P 35/00* (2006.01)
(58) Field of Classification Search
  USPC .......................................................... 514/475
  See application file for complete search history.

(56) References Cited

FOREIGN PATENT DOCUMENTS

| WO | 2014/169356 A1 | 10/2014 |
| WO | 2016/009017 A1 | 1/2016 |
| WO | 2016/057898 A1 | 4/2016 |

OTHER PUBLICATIONS

Adams et al., "Big opportunities for small molecules in immuno-oncology," Nature Reviews Drug Discovery 14, 603-622, 2015.
Anel et al., "Protein kinase C-θ (PKC-θ) in natural killer cell function and anti-tumour immunity," Frontiers in Immunology 3, 187,2012.
Beyaert et al., "Molecular mechanisms of tumor necrosis factor-induced cytotoxicity. What we do understand and what we do not," FEBS Letters 340:9-16, 1994.
Bos et al., "CD4+ T-cell help in the tumor milieu is required for recruitment and cytolytic function of CD8+ T lymphocytes," Cancer Research 70: 8368-8377, 2010.
Boyle et al., "Intra-Lesional Injection of the Novel PKC Activator EBC-46 Rapidly Ablates Tumors in Mouse Models", pp. 1-12, Oct. 2014.
Brezar et al, "PKC-Theta in regulatory and effector T-cell functions," Frontiers in Immunology 6, 530, 2015.
Burkholder et al., "Tumor-induced perturbations of cytokines and immune cell networks," BBA—Reviews on Cancer. 1845: 182-201, 2014.
Chan et al., "Detection of necrosis by release of lactate dehydrogenase (LDH) activity," Methods Molecular Biology 979: 65-70, 2013.
Cohen et al., "CD4+ T cells in adoptive immunotherapy and the indirect mechanism of tumor rejection," Critical Reviews Immunology 2: 85-95, 2000.
Cullen et al., "Investigating a naturally occurring small molecule, EBC-46, as an immunotherapy agent to help treat cancer" Eur. J. Cancer, 69, Suppl, p. S153, Abstract No. 468, 2016.
Denardo et al., "Interactions between lymphocytes and myeloid cells regulate pro-versus anti-tumor immunity," Cancer and Metastasis Reviews 29: 309-316, 2010.
Dyer et al., "Oncolytic group B enadenotucirev mediates non-apoptotic cell death with membrane disruption and release of inflammatory mediators," Molecular Therapy Oncolytics. 4: 18-30, 2016.
Fridman et al., "The immune contexture in human tumours: impact on clinical outcome," Nature Reviews Cancer 12: 298-306, 2012.
Friedman et al, "Treatment of the Immune-Related Adverse Effects of Immune Checkpoint Inhibitors", JAMA Oncology, 2(10), 1346, 2016, Abstract only.
Gabrilovic et al., "Coordinated regulation of myeloid cells by tumours," Nature Reviews Immunology 12: 253-268, 2012.
Galluzzi et al., "Immunogenic cell death in cancer and infectious disease," Nature Reviews Immunology 17: 97-111, 2017.
Garg et al., "Pathogen response-like recruitment and activation of neutrophils by sterile immunogenic dying cells drives neutrophil-mediated residual cell killing," Cell Death Differentiation. 2017. Advance online publication Feb. 24, 2017.
Gomez-Cadena et al., "Immune-system-dependent anti-tumour activity of a plant-derived polyphenol rich fraction in a melanoma mouse model," Cell Death and Disease 7: e2243, 2016.
Grosso et al., "CTLA-4 blockade in tumor models: an overview of preclinical and translational research", 2014, Abstract.
Guermonprez et al., "Antigen presentation and T cell stimulation by dendritic cells," Annual Review of Immunology 20: 621-667, 2002.

Haabeth et al., "Inflammation driven by tumour-specific Th1 cells protects against B-cell cancer," Nature Communications 2: 240, 2011.
Haabeth et al., "A model for cancer-suppressive inflammation," OncoImmunology. 1 (7): 1146-1155, 2012.
Haabeth et al., "Interleukin-1 is required for cancer eradication mediated by tumor-specific Th1 cells," OncoImmunology 5 (1): e1039763, 2016.
Hori et al., "Role of tumor necrosis factor and interleukin 1 in gamma-interferon-promoted activation of mouse tumoricidal macrophages," Cancer Research 49:2606-2614, 1989.
Hu-Lieskovan et al., "New combination strategies using Programmed Cell Death 1/Programmed Cell Death Ligand 1 checkpoint inhibitors as a backbone," The Cancer Journal 23, 10-22, 2017.
Kang et al., "PKCβ modulates antigen receptor signaling via regulation of Btk membrane localization," EMBO J 20, 5692-5702, 2001.
Kepp et al., "Clinical evidence that immunogenic cell death sensitizes to PD-1/PD-L1 blockage," OncoImmunology, vol. 8, No. 10, 2019.
Kim et al., "Mitochondrial permeability transition: a common pathway to necrosis and apoptosis," Biochemical Biophysical Research Communications 304: 463-470, 2003.
Knutson et al., "Tumor antigen-specific T helper cells in cancer immunity and immunotherapy," Cancer Immunol Immunother, 54:721-728, 2005.
Kolaczkowska et al., "Neutrophil recruitment and function in health and inflammation," Nature Reviews Immunology 13: 159-175, 2013.
Kroemer et al., "Immunogenic cell death in cancer therapy," Annual Reviews Immunology 31: 51-72, 2013.
Li et al., "G-CSF is a key modulator of MDSC and could be a potential therapeutic target in colitis-associated colorectal cancers," Protein Cell 7: 130-140, 2016.
Lim et al., "Protein kinase C in the immune system: from signaling to chromatin regulation," Immunology 146, 508-522, 2015.
Mahoney et al., "Combination cancer immunotherapy and new immunomodulatory targets," Nature Reviews Drug Discovery 14, 561-585, 2015.
Merad et al., "The Dendritic Cell Lineage: Ontogeny and Function of Dendritic Cells and Their Subsets in the Steady State and the Inflamed Setting," Annual Review of Immunology 31: 563-604, 2013.
Msaouel et al., "Immune Checkpoint Therapy in Head and Neck Cancers," The Cancer Journal. 22: 108-116, 2016.
Neuzillet et al., "Targeting the TGFβ pathway for cancer therapy," Pharmacology & Therapeutics 147: 22-31, 2015.
O'Brien et al., "Local tumour ablative therapies: Opportunities for maximising immune engagement and activation," BBA Reviews Cancer 1846: 510-523, 2014.
O'Donnell et al., "Resistance to PD1/PDL1 checkpoint inhibition," Cancer Treatment Reviews 52: 71-81, 2017.
Pages et al., "Immune infiltration in human tumors: a prognostic factor that should not be ignored," Oncogene, 29: 1093-1102, 2010.
Pfeifhofer et al., "Defective IgG2a/2b Class Switching in PKCα $^{-/-}$ Mice," Journal of Immunology 176, 6004-6011, 2006.
Qu et al., "Expansion and functions of myeloid-derived suppressor cells in the tumour microenvironment," Cancer Letters 380: 253-256, 2016.
Ribas et al., "Oncolytic Virotherapy Promotes Intratumoral T Cell Infiltration and Improves Anti-PD-1 Immunotherapy," Cell 170(6):1109-19.e10, 2017.
Senovilla et al., "Trial watch: prognostic and predictive value of the immune infiltrate in cancer," Oncoimmunology 1: 1323-1343, 2012.
Serrano-Del Valle et al., "Immunogenic Cell Death and Immunotherapy of Multiple Myeloma," Frontiers in Cell and Developmental Biology, 7, Article 50, 2019.
Sharma et al., "The future of immune checkpoint therapy," Science. 348(6230):56-61, 2015.
Smyth et al., "Combination cancer immunotherapies tailored to the tumour microenvironment," Nature Reviews Clinical Oncology 13, 143-158, 2015.

(56) References Cited

OTHER PUBLICATIONS

Sugarman et al., "Recombinant human tumor necrosis factor-alpha: effects on proliferation of normal and transformed cells in vitro," Science 230:943-945, 1985.
Wang et al., "Therapeutic Strategies to remodel immunologically cold tumors", Clinical & Translational Immunology, e1226 doi: 10.1002/cti2.1226, 2020.
Workenhe et al., "Immunogenic HSV-mediated oncolysis shapes the antitumor immune response and contributes to therapeutic efficacy," Molecular therapy: the journal of the American Society of Gene Therapy. 22: 123-31, 2014.
Yamazaki et al., "PT-112 induces immunogenic cell death and synergizes with immune checkpoint blockers in mouse tumor models," OncoImmunology, vol. 9, No. 1, 2020.
Zahavi et al., "Targeting Multiple Receptors to Increase Checkpoint Blockade Efficacy", pp. 1-11, 2019.
Mali et al., "*Baliospermum montanum* (Danti): Ethnobotany phytochemisty and pharmacology—A review", International Journal of Green Pharmacy, Oct.-Dec. 2008, pp. 194-199.

\* cited by examiner

B16-F10-OVA

COMBINATION THERAPY FOR THE TREATMENT OR PREVENTION OF TUMOURS

FIELD OF THE INVENTION

The present invention relates to a combination therapy for tumours comprising the administration of an epoxytigliane compound and an immune checkpoint inhibitor. Pharmaceutical compositions and kits containing epoxytigliane compounds and immune checkpoint inhibitors are also described.

BACKGROUND OF THE INVENTION

Epoxytiglienone compounds have potent anti-tumour activity. When administered intratumourally, epoxytiglienones initiate rapid haemorrhagic necrosis of the tumour mass by directly disrupting tumour vasculature (Boyle et al. 2014). To date, there is no evidence that localised administration of epoxytiglienone compounds has systemic effects on bystander or more distant tumours and it is considered that the intratumourally delivered epoxytiglienone compounds act primarily at the treatment site. As a consequence, each tumour must be treated individually.

Immunotherapies for treating cancer are gaining wide acceptance in the clinic. In particular, immune checkpoint inhibitors (ICI) have demonstrated promise in a range of malignancies including advanced metastatic melanoma, non-small cell lung cancer, renal cancer, bladder cancer, and Hodgkin's lymphoma. ICIs are molecules (typically monoclonal antibodies) that block the action of proteins that allow tumour cells to evade, suppress or resist the host immune system, especially the T cells that are specific for tumour antigens. Current approved T cell checkpoint inhibitors enhance the antitumour immune response through distinctly different mechanisms of action. For example, cytotoxic T-lymphocyte-associated antigen 4 (CTLA4) blockade predominantly enhances T cell activation during the priming phase of the immune response, whereas programmed cell death protein 1 (PD1) blockade appears to release exhausted but otherwise activated effector T cell populations and reduce regulatory T (Treg) cell function.

While ICIs can elicit remarkable and durable responses in advanced cancer patients, these positive responses are limited to a small proportion of the total patient population (Hu-Lieskovan et al. 2017). Consequently, approaches that combine ICIs with other treatment modalities (e.g. radiation therapy, chemotherapy, oncolytic viruses, cancer vaccines) that could stimulate a host immune response provide an attractive and clinically feasible approach to overcome intrinsic and acquired resistance to cancer immunotherapy, and to potentially extend clinical success to a broader range of patients (Smyth et al. 2015).

One such approach is to combine ICIs with small molecule chemotherapeutics (delivered either systemically or intratumourally) that may modulate immune responses by (1) reducing overall tumour burden, (2) potentiating the anti-tumour response by exposing neo-antigen during tumour necrosis and/or (3) directly affecting tumour stromal cells (Adams et al. 2015; Mahoney et al. 2015; O'Brien et al. 2014).

The present invention is predicated, at least in part, on the discovery that some epoxytiglien-3-one compounds can stimulate an immune response that can work synergistically with immune checkpoint blockade to provide a therapy not only for the tumour being treated but also other tumours that may be present in the subject being treated.

SUMMARY OF THE INVENTION

In one aspect, the present invention relates to a method of treating at least one tumour in a subject comprising administering to a subject, an epoxytigliane compound or a pharmaceutically acceptable salt thereof and an immune checkpoint inhibitor.

In another aspect of the present invention there is provided a method of treating or preventing a bystander tumour in a subject comprising administering to a subject in need thereof, an epoxytigliane compound or a pharmaceutically acceptable salt thereof and an immune checkpoint inhibitor; wherein the epoxytigliane compound is administered locally to a tumour other than the bystander tumour.

In another aspect of the invention there is provided a use of an epoxytigliane compound or a pharmaceutically acceptable salt thereof and an immune checkpoint inhibitor in the manufacture of a medicament for treating a tumour.

In yet another aspect of the invention there is provided a use of an epoxytigliane compound or a pharmaceutically acceptable salt thereof in the manufacture of a medicament for treating a tumour, wherein the medicament is for administration in combination with an immune checkpoint inhibitor.

In a further aspect of the invention, there is provided a use of an immune checkpoint inhibitor in the manufacture of a medicament for treating a tumour, wherein the medicament is for administration in combination with an epoxytigliane compound or a pharmaceutically acceptable salt thereof.

In another aspect of the invention there is provided a use of an epoxytigliane compound or a pharmaceutically acceptable salt thereof and an immune checkpoint inhibitor in the manufacture of a medicament for treating or preventing a bystander tumour.

In yet a further aspect of the invention there is provided a use of an epoxytigliane compound or a pharmaceutically acceptable salt thereof in the manufacture of a medicament for treating or preventing a bystander tumour, wherein the medicament is for administration in combination with an immune checkpoint inhibitor.

In another aspect of the present invention, there is provided a use of an immune checkpoint inhibitor in the manufacture of a medicament for treating or preventing a bystander tumour, wherein the medicament is for administration in combination with an epoxytigliane compound or a pharmaceutically acceptable salt thereof.

In yet another aspect of the invention there is provided an epoxytigliane compound or a pharmaceutically acceptable salt thereof in combination with an immune checkpoint inhibitor for treating a tumour or treating or preventing a bystander tumour.

In another aspect of the present invention there is provided a pharmaceutical composition comprising an epoxytigliane compound or a pharmaceutically acceptable salt thereof and an immune checkpoint inhibitor, optionally together with one or more pharmaceutically acceptable carriers.

In a further aspect of the present invention there is provided a kit comprising an epoxytigliane compound or a pharmaceutically acceptable salt thereof and an immune checkpoint inhibitor.

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The term "alkyl" refers to optionally substituted linear and branched hydrocarbon groups having 1 to 20 carbon atoms. Where appropriate, the alkyl group may have a specified number of carbon atoms, for example, —$C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, 2-methylpentyl, 3-methylpentyl, 4-methylpentyl, 2-ethylbutyl, 3-ethylbutyl, heptyl, octyl, nonyl, decyl, undecyl, dodecyl, tridecyl, tetradecyl and pentadecyl.

The term "alkenyl" refers to optionally substituted, unsaturated linear or branched hydrocarbons, having 2 to 20 carbon atoms and having at least one double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-1,3-diene, hex-1,3-diene, non-1,3,5-triene and the like.

The term "alkynyl" refers to optionally substituted unsaturated linear or branched hydrocarbons, having 2 to 20 carbon atoms, having at least one triple bond. Where appropriate, the alkynyl group may have a specified number of carbon atoms, for example, $C_2$-$C_6$ alkynyl which includes alkynyl groups having 2, 3, 4, 5 or 6 carbon atoms in linear or branched arrangements. Non-limiting examples include ethynyl, propynyl, butynyl, pentynyl and hexynyl.

The terms "cycloalkyl" and "carbocyclic" refer to optionally substituted saturated or unsaturated mono-cyclic, bicyclic or tricyclic hydrocarbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

"Aryl" means a $C_6$-$C_{14}$ membered monocyclic, bicyclic or tricyclic carbocyclic ring system having up to 7 atoms in each ring, wherein at least one ring is aromatic. Examples of aryl groups include, but are not limited to, phenyl, naphthyl, tetrahydronaphthyl, indanyl and biphenyl. The aryl may comprise 1-3 benzene rings. If two or more aromatic rings are present, then the rings may be fused together, so that adjacent rings share a common bond.

Each alkyl, alkenyl, alkynyl, cycloalkyl or aryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, oxo (=O), —OH, —SH, $C_{1-6}$alkylO—, $C_{2-6}$alkenylO—, $C_{3-6}$cycloalkylO—, $C_{1-6}$alkylS—, $C_{2-6}$alkenylS—, $C_{3-6}$cycloalkylS—, —$CO_2$H, —$CO_2C_{1-6}$alkyl, —$NH_2$, —NH($C_{1-6}$alkyl), —N($C_{1-6}$alkyl)$_2$, —NH(phenyl), —N(phenyl)$_2$, —CN, —$NO_2$, -halogen, —$CF_3$, —$OCF_3$, —$SCF_3$, —$CHF_2$, —$OCHF_2$, —$SCHF_2$, -phenyl, —$C_{1-6}$alkylphenyl, —Ophenyl, —C(O)phenyl, —C(O)$C_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —$CO_2$H, —$CO_2CH_3$, —C(O)$CH_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The epoxytigliane compounds may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will also be recognised that the epoxytigliane compounds may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be obtained by isolation from natural sources, by asymmetric synthesis, for example using chiral intermediates, or by chiral resolution. The compounds of the invention may exist as geometrical isomers. The invention also relates to compounds in substantially pure cis (Z) or trans (E) forms or mixtures thereof.

The compounds of the present invention may be obtained by isolation from a plant or plant part, or by derivatisation of the isolated compound, or by derivatisation of a related compound. Isolation procedures and derivatisation procedures may be found in WO 2007/070985 and WO2014/169356.

The term "epoxytigliane compound" refers to a compound having the following basic carbon cyclic structure:

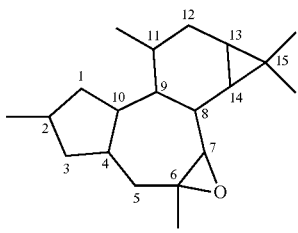

The compounds have a tricyclo[9.3.0.0]tetradecane system with a fused cyclopropane ring appended to the six membered ring. The epoxide is fused to the seven membered ring in the 6,7-position.

One example of an epoxytigliane compound is an epoxytiglien-3-one compound. The term "epoxytiglien-3-one compound" refers to a compound having an epoxytigliane structure defined above where the five membered ring has a 1,2-ene-3-one structure:

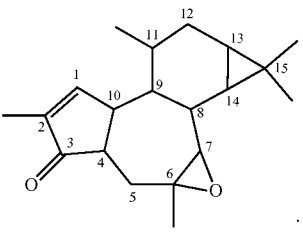

As used herein the term "bystander tumour" refers to a tumour other than the tumour which is treated with the epoxytigliane compound. The bystander tumour may be a primary tumour or a metastatic tumour.

The term "in combination with" as used herein refers to the epoxytigliane compound and the ICI being administered in a single composition, or separately, either simultaneously or sequentially. The epoxytigliane compound and the ICI may be administered at different times and different frequencies but in combination they exert biological effects at the same time or at overlapping times. For example, the ICI is administered so that it has an effect on immune response when the epoxytigliane compound is administered.

Methods of Treatment

The present invention relates to methods of treating tumours, including bystander tumours, the method comprising the administration of an epoxytigliane compound or a pharmaceutically acceptable salt thereof in combination with an immune checkpoint inhibitor (ICI). The invention also relates to methods of preventing bystander tumours comprising the administration of an epoxytigliane compound or a pharmaceutically acceptable salt thereof in combination with an ICI.

In some embodiments, the tumour being treated is a tumour to which the epoxytigliane compound may be delivered in a localised way directly to the tumour. In particular embodiments, the tumour is a cutaneous tumour or subcutaneous tumour or a tumour accessible from the outside of the body, for example, a tumour that is palpable. In other embodiments, the tumour is an internal tumour. In some embodiments where the tumour is an internally located tumour, the localised delivery is achieved during surgery when the tumour is exposed and able to be injected with the epoxytigliane compound. In other embodiments, the tumour is internally located and the epoxytigliane compound is delivered by injection guided by an imaging technique, for example, guided by endoscopic ultrasound or by stereotactic imaging.

In some embodiments, the epoxytigliane compound is delivered to one or more tumours systemically.

In some embodiments, the tumour is a benign tumour. In other embodiments, the tumour is a malignant tumour. In some embodiments, the tumour is a primary tumour and in other embodiments, the tumour is a metastatic tumour. Examples of cutaneous tumours include seborrheic keratosis, actinic keratosis, basal cell carcinoma (BCC) including nodular BCC, superficial BCC, infiltrative BCC and micronodular BCC, squamous cell carcinoma, including in-situ squamous cell carcinoma and invasive squamous cell carcinoma, melanoma including superficial spreading melanoma, nodular melanoma, lentigo maligna melanoma, acral lentginous melanoma and desmoplastic/neutropic melanoma, cutaneous B cell lymphoma and cutaneous T cell lymphoma. Examples of subcutaneous tumours include angiokeratoma, pyogenic granuloma, cherry angioma, glomus tumour, angiosarcoma, karposi sarcoma, Ewings sarcoma, malignant fibrous histiocytoma, leiomyosarcoma, rhabdomyosarcoma, liposarcoma, synovial sarcoma, stromal sarcoma, gastrointestinal stromal sarcoma, malignant peripheral nerve sheath tumour, primitive neuroectodermal tumour, neurofibroma, Merkel cell carcinoma, dermatofibroma, fibrosarcoma, epithelioid sarcoma and mastocytoma (mast cell tumour).

The internal tumour may be any tumour that is accessible to injection during surgery or by guided injection or one that may be treated with systemically administered epoxytigliane and include tumours of the brain, lung, colon, epidermoid, squamous cell, bladder, stomach, pancreas, breast, head, neck, renal system, kidney, liver, ovary, prostate, uterus, oesophagus, testicles, cervix, vagina, thyroid or skin.

The bystander tumour may be any tumour other than the tumour being treated with the epoxytigliane compound. For example, the bystander tumour may be a second cutaneous or subcutaneous tumour or it may be a tumour in another organ or tissue. Examples of bystander tumours include tumours of the brain, lung, colon, epidermoid, squamous cell, bladder, stomach, pancreas, breast, head, neck, renal system, kidney, liver, ovary, prostate, uterus, oesophagus, testicles, cervix, vagina, thyroid or skin.

In some embodiments, the bystander tumour is an additional primary tumour and in other embodiments the bystander tumour is a metastatic tumour.

In some embodiments, the tumour being treated with the epoxytigliane compound is a primary tumour and the bystander tumour is a metastatic tumour. In some embodiments, the tumour being treated with the epoxytigliane compound is a metastatic tumour and the bystander tumour is a primary tumour. In some embodiments, both the tumour being treated with the epoxytigliane compound and the bystander tumour are primary tumours. In some embodiments, both the tumour being treated with the epoxytigliane compound and the bystander tumour are metastatic tumours.

In some embodiments, the combination therapy prevents the bystander tumour occurring or delays the occurrence of the bystander tumour. In some embodiments, the combination therapy reduces the size of the bystander tumour.

Epoxytigliane Compounds

In some embodiments, the epoxytigliane compound is a 6,7-epoxytigliane compound.

In some embodiments, the epoxytigliane compound is an epoxytigli-1,2-en-3-one compound. In some embodiments, the epoxytigliane compound is a 6,7-epoxytigli-1,2-en-3-one compound.

In some embodiments, the epoxytigliane compound is a compound of formula (I):

(I)

or a geometric isomer or stereoisomer or a pharmaceutically acceptable salt thereof; wherein $R_1$ is hydrogen or $C_{1-6}$alkyl;
$R_2$ is —OH or —$OR_9$;
$R_3$ is —OH or —$OR_9$;
$R_4$ and $R_5$ are independently selected from hydrogen and $C_{1-6}$alkyl;
$R_6$ is hydrogen or —$R_{10}$;
$R_7$ is hydroxy or —$OR_{10}$;
$R_8$ is hydrogen or $C_{1-6}$alkyl;
$R_9$ is —$C_{1-20}$alkyl, —$C_{2-20}$alkenyl, —$C_{2-20}$alkynyl, —C(O)$C_{1-20}$alkyl, —C(O)$C_{2-20}$alkenyl, —C(O)$C_{2-20}$alkynyl, —C(O)cycloalkyl, —C(O)$C_{1-10}$alkylcycloalkyl; —C(O)$C_{2-10}$alkenylcycloalkyl, —C(O)$C_{2-10}$alkynylcycloalkyl, —C(O)aryl, —C(O)$C_{1-10}$alkylaryl, —C(O)$C_{2-10}$alkenylaryl, —C(O)$C_{2-10}$alkynylaryl, —C(O)$C_{1-10}$alkylC(O)$R_{11}$, —C(O)$C_{2-10}$alkenylC(O)$R_{11}$, —C(O)$C_{2-10}$alkynylC(O)$R_{11}$, —C(O)$C_{1-10}$alkylCH($OR_{11}$)($OR_{11}$), —C(O)$C_{2-10}$alkenylCH($OR_{11}$)($OR_{11}$), —C(O)$C_{2-10}$alkynylCH($OR_{11}$)($OR_{11}$), —C(O)$C_{1-10}$alkyl$SR_{11}$, —C(O)$C_{2-10}$alkenyl$SR_{11}$, —C(O)$C_{2-10}$alkynyl$SR_{11}$, —C(O)$C_{1-10}$alkylC(O)$OR_{11}$, —C(O)$C_{2-10}$alkenylC(O)$OR_{11}$, —C(O)$C_{2-10}$alkynylC(O)$OR_{11}$, —C(O)$C_{1-10}$alkylC(O)$SR_{11}$, —C(O)$C_{2-10}$alkenylC(O)$SR_{11}$, —C(O)$C_{2-10}$alkynylC(O)$SR_{11}$, —C(O)$C_{1-10}$alkyl—[epoxide]—$R_{11}$, —C(O)$C_{2-10}$alkenyl—[epoxide]—$R_{11}$, or —C(O)$C_{2-10}$alkynyl—[epoxide]—$R_{11}$;

$R_{10}$ is —$C_{1-6}$alkyl, —$C_{2-6}$alkenyl, —$C_{2-6}$alkynyl, —C(O)$C_{1-6}$alkyl, —C(O)$C_{2-6}$alkenyl, —C(O)$C_{2-6}$alkynyl, —C(O)aryl, —C(O)$C_{1-6}$alkylaryl, —C(O)$C_{2-6}$alkenylaryl, —C(O)$C_{2-6}$alkynylaryl; and $R_{11}$ is hydrogen, —$C_{1-10}$alkyl, —$C_{2-10}$alkenyl, —$C_{2-10}$alkynyl, cycloalkyl or aryl; wherein each alkyl, alkenyl, alkynyl, cycloalkyl or aryl group is optionally substituted.

In some embodiments, the epoxytigliane compound of formula (I) is a compound of formula (II):

(II)

or a geometric isomer or stereoisomer or a pharmaceutically acceptable salt thereof, where $R_6$, $R_7$ and $R_9$ are as defined for formula (I).

In particular embodiments of formulae (I) or (II), one or more of the following applies: $R_1$ is —$C_{1-3}$alkyl, especially —$CH_3$;

$R_2$ is —OC(O)$C_{1-20}$alkyl, —OC(O)$C_{2-20}$alkenyl, —OC(O)$C_{2-20}$alkynyl, —OC(O)cycloalkyl, —OC(O)$C_{1-10}$alkylcycloalkyl; —OC(O)$C_{2-10}$alkenylcycloalkyl, —OC(O)$C_{2-10}$alkynylcycloalkyl, —OC(O)aryl, —OC(O)$C_{1-10}$alkylaryl, —OC(O)$C_{2-10}$alkenylaryl, —OC(O)$C_{2-10}$alkynylaryl, —OC(O)$C_{1-10}$alkylC(O)$R_{11}$, —OC(O)$C_{2-10}$alkenylC(O)$R_{11}$, —OC(O)$C_{2-10}$alkynylC(O)$R_{11}$, —OC(O)$C_{1-10}$alkylCH($OR_{11}$)($OR_{11}$), —OC(O)$C_{2-10}$alkenylCH($OR_{11}$)($OR_{11}$), —OC(O)$C_{2-10}$alkynylCH($OR_{11}$)($OR_{11}$), —OC(O)$C_{1-10}$alkyl$SR_{11}$, —OC(O)$C_{2-10}$alkenyl$SR_{11}$, —OC(O)$C_{2-10}$alkynyl$SR_{11}$, —OC(O)$C_{1-10}$alkylC(O)$OR_{11}$, —OC(O)$C_{2-10}$alkenylC(O)$OR_{11}$, —OC(O)$C_{2-10}$alkynylC(O)$OR_{11}$, —OC(O)$C_{1-10}$alkylC(O)$SR_{11}$, —OC(O)$C_{2-10}$alkenylC(O)$SR_{11}$ or —OC(O)$C_{2-10}$alkynylC(O)$SR_{11}$; especially —OC(O)$C_{1-20}$alkyl, —OC(O)$C_{2-20}$alkenyl, —OC(O)$C_{2-20}$alkynyl, —OC(O)cycloalkyl, —OC(O)$C_{1-10}$alkylcycloalkyl; —OC(O)$C_{2-10}$alkenylcycloalkyl, —OC(O)$C_{2-10}$alkynylcycloalkyl or —OC(O)aryl; more especially —OC(O)$C_{1-20}$alkyl, —OC(O)$C_{2-20}$alkenyl or —OC(O)$C_{2-20}$alkynyl;

$R_3$ is —OC(O)$C_{1-20}$alkyl, —OC(O)$C_{2-20}$alkenyl, —OC(O)$C_{2-20}$alkynyl, —OC(O)cycloalkyl, —OC(O)$C_{1-10}$alkylcycloalkyl; —OC(O)$C_{2-10}$alkenylcycloalkyl, —OC(O)$C_{2-10}$alkynylcycloalkyl, —OC(O)aryl, —OC(O)$C_{1-10}$alkylaryl, —OC(O)$C_{2-10}$alkenylaryl, —OC(O)$C_{2-10}$alkynylaryl, —OC(O)$C_{1-10}$alkylC(O)$R_{11}$, —OC(O)$C_{2-10}$alkenylC(O)$R_{11}$, —OC(O)$C_{2-10}$alkynylC(O)$R_{11}$, —OC(O)$C_{1-10}$alkylCH($OR_{11}$)($OR_{11}$), —OC(O)$C_{2-10}$alkenylCH($OR_{11}$)($OR_{11}$), —OC(O)$C_{2-10}$alkynylCH($OR_{11}$)($OR_{11}$), —OC(O)$C_{1-10}$alkyl$SR_{11}$, —OC(O)$C_{2-10}$alkenyl$SR_{11}$, —OC(O)$C_{2-10}$alkynyl$SR_{11}$, —OC(O)$C_{1-10}$alkylC(O)$OR_{11}$, —OC(O)$C_{2-10}$alkenylC(O)$OR_{11}$, —OC(O)$C_{2-10}$alkynylC(O)$OR_{11}$, —OC(O)$C_{1-10}$alkylC(O)$SR_{11}$, —OC(O)$C_{2-10}$alkenylC(O)$SR_{11}$ or —OC(O)$C_{2-10}$alkynylC(O)$SR_{11}$; especially —OC(O)$C_{1-20}$alkyl, —OC(O)$C_{2-20}$alkenyl, —OC(O)$C_{2-20}$alkynyl, —OC(O)cycloalkyl, —OC(O)$C_{1-10}$alkylcycloalkyl; —OC (O)C$_{2-10}$alkenylcycloalkyl, —OC(O)C$_{2-10}$alkynylcycloalkyl or —OC(O)aryl; more especially —OC(O)C$_{1-20}$alkyl, —OC(O)C$_{2-20}$alkenyl or —OC(O)C$_{2-20}$alkynyl;

R$_4$ and R$_5$ are independently selected from —C$_{1-3}$alkyl, especially —CH$_3$;

R$_6$ is hydrogen, —C(O)C$_{1-6}$alkyl, —C(O)C$_{2-6}$alkenyl, —C(O)C$_{2-6}$alkynyl or —C(O)aryl; especially hydrogen, —C(O)C$_{1-3}$alkyl, —C(O)C$_{2-3}$alkenyl or —C(O)C$_{2-3}$alkynyl, more especially hydrogen or —C(O)CH$_3$;

R$_7$ is hydroxyl, —OC(O)C$_{1-6}$alkyl, —OC(O)C$_{2-6}$alkenyl or —OC(O)C$_{2-6}$alkynyl, especially hydroxyl, —OC(O)C$_{1-3}$alkyl, —OC(O)C$_{2-3}$alkenyl or —OC(O)C$_{2-3}$alkynyl, more especially hydroxyl or —OC(O)CH$_3$; and R$_8$ is —C$_{1-3}$alkyl, especially —CH$_3$.

In some embodiments, the compounds of formulae (I) and/or (II) have stereochemistry as shown in formula (III) below:

(III)

In some embodiments, the epoxide in the 6,7-position is above the plane of the ring system. In other embodiments, the epoxide in the 6,7-position is below the plane of the ring system. In some embodiments, the R$_2$ group in the 12 position is S and in other embodiments, the R$_2$ group in the 12 position is R.

In particular embodiments the epoxytigliane compound is selected from:
12-tigloyl-13-(2-methylbutanoyl)-6,7-epoxy-4,5,9,12,13,20-hexahydroxy-1-tiglien-3-one (Compound 1);
12,13-di-(2-methylbutanoyl)-6,7-epoxy-4,5,9,12,13,20-hexahydroxy-1-tiglien-3-one (Compound 2);
12-hexanoyl-13-(2-methylbutanoyl)-6,7-epoxy-4,5,9,12,13,20-hexahydroxy-1-tiglien-3-one (Compound 3);
12,13-dihexanoyl-6,7-epoxy-4,5,9,12,13,20-hexahydroxy-1-tiglien-3-one (Compound 4);
12-myristoyl-13-(2-methylbutanoyl)-6,7-epoxy-4,5,9,12,13,20-hexahydroxy-1-tiglien-3-one (Compound 5);
12-tigloyl-13-(2-methylbutanoyl)-6,7-epoxy-4,5,9,12,13-pentahydroxy-20-acetyloxy-1-tiglien-3-one (Compound 6);
12-myristoyl-13-acetyloxy-6,7-epoxy-4,5,9,12,13,20-hexahydroxy-1-tiglien-3-one (Compound 7);
12-propanoyl-13-(2-methylbutanoyl)-6,7-epoxy-4,5,9,12,13,20-hexahydroxy-1-tiglien-3-one (Compound 8);
12,13-ditigloyl-6,7-epoxy-4,5,9,12,13,20-hexahydroxy-1-tiglien-3-one (Compound 9); and
12-(2-methylbutanoyl)-13-tigloyl-6,7-epoxy-4,5,9,12,13,20-hexahydroxy-1-tiglien-3-one (Compound 10).

Immune Checkpoint Inhibitor (ICI)

The ICI may be any molecule that inhibits immune cell or cancer cell proteins that block immune responses in the immune cell, especially where the immune cell is a T cell or a natural killer cell (NK cell). Examples of immune cell and tumour cell proteins include Programmed Death 1 (PD-1) on T cells which binds PD-L1 of a tumour cell to block immune response of the T cell against the tumour cell and Cytotoxic T-Lymphocyte-Associated protein 4 (CTLA-4) protein on a T cell which binds B7-1/B7-2 protein on a cancer cell to block immune response of the T cell against the tumour cell. Therefore ICIs include molecules that bind to or block the interaction of PD-1 with PD-L1/PDL2 or CTLA-4 with B7-1/B7-2. Other immune cell proteins that block immune responses in immune cells and may be modulated to prevent their action include Adenosine A2A receptor, B7-H3, B7-H4, indoleamine 2,3-dioxygenase (IDO), Killer-cell Immunoglobulin like receptor (KIR), Lymphocyte Activation Gene-3 (LAG3), T cell immunoreceptor with IG and ITIM domains (TIGIT), T-cell immunoglobulin and mucin-domain containing-3 (TIM-3), CD96 and V-domain Immunoglobulin Suppressor of T cell Activation (VISTA).

Examples of ICIs include, but are not limited to antagonists of PD-1, PD-L1, PD-L2, CTLA-4, B7-1/B7-2 protein, Adenosine A2A receptor, B7-H3, B7-H4, IDO, KIR, LAG3, TIM-3, TIGIT, CD96 and VISTA, especially antagonists of PD-1, PD-L1, CTLA-4 or B7-1/B7-2 protein, more especially antagonists of PD-1 or CTLA-4. In particular embodiments, the antagonist is an antibody for the immune checkpoint protein, for example, Anti-PD-1 antibody or Anti-CTLA-4 antibody. In other embodiments, a particular antagonist is an antagonist of IDO.

Compositions

While the epoxytigliane compounds or pharmaceutically acceptable salts thereof and ICIs, may be administered neat, it may be more convenient to administer the epoxytigliane compounds and ICIs in the form of one or more pharmaceutical compositions, each together with a pharmaceutically acceptable carrier, diluent and/or excipient.

Dosage form and rates for pharmaceutical use and compositions are readily determinable by a person of skill in the art.

In particular embodiments, the epoxytigliane compound is formulated for administration directly onto or into the tumour being treated. In some embodiments, the epoxytigliane compound is formulated for topical administration in the form of a gel, ointment, lotion, cream or transdermal patch that may be applied directly onto the tumour being treated. In other embodiments, the epoxytigliane compound is formulated for injection, especially intratumoural injection where the compound is injected into one or more places in a tumour.

The ICI may be administered in any means that is able to deliver the molecule systemically or locally. In particular embodiments, when the ICI is an antibody, the molecule is conveniently delivered by injection, for example, intravenous, intraarticular, intramuscular, intradermal, subcutaneous or intraperitoneal injection. The ICI may also be formulated for local delivery by injection, for example, intratumourally. Pharmaceutically acceptable carriers and acceptable carriers for systemic or local administration may also be incorporated into the compositions of ICIs.

In some embodiments, the epoxytigliane compound and the ICI are delivered separately, either simultaneously or sequentially. In other embodiments, the epoxytigliane compound and the ICI are delivered in a single composition, for example, a single composition suitable for intratumoural delivery or a single composition formulated for systemic delivery.

In another aspect of the present invention there is provided a pharmaceutical composition comprising an epoxytigliane compound or a pharmaceutically acceptable salt thereof and an immune checkpoint inhibitor, optionally together with one or more pharmaceutically acceptable carriers.

Suitably, the pharmaceutical composition(s) comprise a pharmaceutically acceptable excipient or an acceptable excipient. By "pharmaceutically acceptable excipient" is meant a solid or liquid filler, diluent or encapsulating substance that may be safely used. Depending upon the particular route of administration, a variety of carriers, well known in the art may be used. These carriers or excipients may be selected from a group including sugars, starches, cellulose and its derivatives, cyclodextrins, malt, gelatine or other gelling agents, polymers, talc, calcium sulphate, vegetable oils, synthetic oils, alcohols and/or polyols, alginic acid, phosphate buffered solutions, emulsifiers, isotonic saline, and pyrogen-free water.

Liquid form preparations include solutions, suspensions, and emulsions, for example, water or water-propylene glycol solutions. For example, parenteral injection liquid preparations can be formulated as solutions in aqueous 1,2-propanediol, dimethylsulfoxide (DMSO), aqueous solutions of gamma cyclodextrin or 2-hydroxypropyl-beta-cyclodextrin, saline solution or polyethylene glycol solution, with or without buffer. A preferred range of pH is 3.0-4.5. Suitable buffers buffer the preparation at pH 3.5-4.5 and include, but are not limited to, acetate buffer and citrate buffer.

The compositions of epoxytigliane compound and/or ICI may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, gels or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical compositions of epoxytigliane compound and/or ICI suitable for administration may be presented in discrete units such as syringes, vials, tubes or sachets each containing a predetermined amount of one or more pharmaceutically active compounds or extracts of the invention, as a powder or granules or as a solution or a suspension in an aqueous liquid, a cyclodextrin solution, a non-aqueous liquid, an oil-in-water emulsion or a water-in-oil emulsion or as a solution or suspension in a cream or gel or as a suspension of micro- or nano-particles incorporating an epoxytigliane compound, including but not limited to silica or polylactide micro- or nano-particles. Such compositions may be prepared by any of the method of pharmacy but all methods include the step of bringing into association one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

For topical administration to the epidermis or other organ, the compounds according to the invention may be formulated as gels, ointments, emulsions, pastes, creams or lotions, or as a transdermal patch. Gels may be prepared using suitable thickening agents and adding them to aqueous/alcoholic compositions of compound. Suitable thickening or gelling agents are known in the art, such as the polyvinyl carboxy polymer Carbomer 940. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration also include solutions or suspensions that may be administered topically in the form of a bath or soak solution or a spray or may be absorbed into a dressing.

When the ICI is a small molecule, it may be delivered by any suitable means including oral, topical, rectal, parenteral, sublingual, buccal, intravenous, intraarticular, intra-muscular, intra-dermal, subcutaneous, inhalational, intraocular, intraperitoneal, intracerebroventricular, transdermal and the like as known in the art of pharmacy.

Dosage Regimens

In some embodiments, the epoxytigliane compound is delivered in the same composition as the ICI. However, in particular embodiments, the ICI is administered in a separate composition from the epoxytigliane compound.

In some embodiments, the epoxytigliane compound is administered directly to the tumour, for example by topical administration or by intra-tumoural injection.

In some embodiments, the epoxytigliane compound is administered to the tumour once. In other embodiments, the treated tumour is monitored and further administration of epoxytigliane compound may be required if the tumour does not fully respond to the treatment. In embodiments where the tumour is treated topically, the epoxytigliane compound may be administered on a number of occasions over a period of time, for example, daily for a week, or once a week for 4 to 10 weeks. A person skilled in the art, monitoring the subject being treated would be able to determine an appropriate dosage schedule, which may vary depending on the response to the treatment.

In some embodiments, the ICI is administered at least once, prior to or simultaneously or sequentially with the epoxytigliane compound. In particular embodiments, multiple doses of ICI are administered over a period of time beginning before or together with administration of the epoxytigliane compound and then continuing after administration of the epoxytigliane compound.

In some embodiments, the ICI is administered more than once and on a regular basis before and after administration of the epoxytigliane compound. In particular embodiments, the ICI is administered before administration of the epoxytigliane compound, sequentially or simultaneously with the administration of the epoxytigliane compound and at least once subsequently to administration of the epoxytigliane compound. For example, the ICI may be administered 1 week to 1 day prior to administration of the epoxytigliane compound, especially 1 to 3 days and more especially about 2 days before the administration of the epoxytigliane compound, the ICI is then administered sequentially or simultaneously with the epoxytigliane compound, either immediately before or immediately after the administration of the epoxytigliane compound, the ICI is then administered one or more times over the next month after administration of the epoxytigliane compound, for example, once a week, once every 5 days, once every 4 days, once every 3 days, every 2 days or every day, especially every 1 to 3 days, more especially every 2 days. Subsequent administration of the ICI may continue such that 1 to 10 doses of ICI are administered after the administration of the epoxytigliane compound, especially 1 to 8 doses, 1 to 6 doses, 1 to 4 doses, 1 to 3 doses or 1 to 2 doses.

In a particular embodiment, the ICI is administered 2 days before the administration of the epoxytigliane compound, sequentially (immediately before or immediately after) with the epoxytigliane compound and then every two days for 6 days following administration of the epoxytigliane compound.

The epoxytigliane compound is administered in an effective amount. An "effective amount" means an amount necessary at least partly to attain the desired response, for example, to reduce the size of the tumour or to destroy the tumour in total. The amount varies depending upon the health and physical condition of the individual to be treated, the taxonomic group of individual to be treated, the formulation of the composition, the size of the tumour, the assessment of the medical situation, and other relevant factors. It is expected that the amount will fall in a relatively broad range that can be determined through routine trials. An effective amount, for example, may lie in the range of about 0.1 ng per kg of body weight to 1 g per kg of body weight per dosage. The dosage is preferably in the range of 1 µg to 0.5 g per kg of body weight per dosage, such as is in the range of 0.1 µg to 100 mg per kg of body weight per dosage. In one embodiment, where the dosage is administered intra-tumourally, the dosage is in the range of 50 ng to 100 mg per kg of body weight, for example 0.1 mg to 5 mg per kg of body weight, 0.1 to 1 mg/kg of body weight, such as 0.25 mg/kg of body weight. In another embodiment, the dosage is in the range of 0.001 mg to 20 mg per dosage, for example, 0.005 mg to 15 mg per dosage, especially 0.05 to 10 mg per dosage, more especially about 0.1 to about 5 mg per dosage. Dosage regimes may be adjusted to provide the optimum therapeutic response. For example, in some embodiments, where administration is intra-tumoural, the epoxytigliane compound is administered once and the progress of treatment monitored. In some embodiments, if the tumour does not completely resolve or if the tumour recurs, a second dose may be administered. In some embodiments, where the administration is topical, the topical compound formulation may be administered directly onto the site of the tumour in the form of a gel, cream, ointment or lotion. The frequency of treatment will depend on the tumour, its size, the subject being treated and the like. In some embodiments, a topical formulation may be applied weekly until the tumour is resolved. In other embodiments, the treatment may be a single treatment and a second treatment only administered if the tumour is not completely resolved.

The ICI may also be administered in an effective amount. Again, the amount of ICI considered to be effective will depend on the subject being treated, their health and physical condition, the number of bystander tumours present, the formulation of the composition and the assessment of the medical situation. It is expected that the amount of ICI will fall within a fairly broad range of amounts. An effective amount may lie in the range of about 0.1 ng/kg to about 500 mg/kg body weight, 100 rig/kg to 100 mg/kg body weight, 1 mg/kg to 50 mg/kg body weight, 1 mg/kg to 20 mg/kg body weight. In another embodiment, the actual dosages may be in the range of from 1 µg to 1 g, for example, 100 µg to 750 mg per dose.

The subject that may be treated with the combination therapy is a mammal, a bird, an aquatic animal such as a fish, or a reptile. In some embodiments, the subject is a human, a laboratory animal such as a mouse, rat or rabbit, a companion animal such as a dog or cat, a working animal such as a horse, donkey and the like, a livestock animal such as a cow, bull, pig, sheep, goat, deer, llama, alpaca and the like, or a captive wild animal such as those in zoos or wildlife parks including lions, leopards, cheetah, elephant, zebra, antelope, giraffe, koala, kangaroo and reptiles such as crocodiles, lizards, snakes and the like, a bird, especially a captive bird, such as a budgerigar or canary, cockatoo, parakeet, macaw, parrot and the like, or a fish, especially a captive fish such as tropical fish (zebra fish, guppy, Siamese fighting fish, clown fish, cardinal tetra and the like), dolphins, whales, and the like. In particular embodiments, the subject is a human or a companion animal.

Kits

The compositions of epoxytigliane compound and ICI may be formulated separately and sold together in a kit or package. Each kit may comprise dosages of each compound to achieve treatment of a tumour and treat or prevent one or more bystander tumours.

In some embodiments, the epoxytigliane composition is formulated for topical administration, such as in a gel, lotion, cream or ointment or is impregnated into a dressing. In other embodiments, the epoxytigliane compound is formulated for injection such as intratumoural injection. In this embodiment, the epoxytigliane formulation may be present in the kit as a liquid ready for uptake into a syringe, as a powder or solid formulation which may be solubilized in a carrier before injection or may be present in the kit in a pre-filled syringe.

Each kit may comprise one or more doses of epoxytigliane compound. In one embodiment, the kit will contain a single dose of epoxytigliane compound in a formulation suitable for intratumoural injection. In another embodiment, the kit will contain a topical formulation of epoxytigliane compound containing multiple doses for application to the tumour.

In some embodiments, the ICI is formulated for parenteral administration in a single bolus dose or in a multiple dose form. For example, the kit may contain the ICI in a pre-filled syringe, as a liquid in a vial ready for uptake into a syringe, or as a solid ready for dissolution before uptake into a syringe. The liquid or solid formulations may be single dose formulations or multiple dose formulations. Alternatively the kit may contain multiple doses of ICI each formulated separately in a prefilled syringe, as a liquid in a vial ready for uptake into a syringe or as a solid ready for dissolution and uptake into a syringe.

The kit may further comprise an insert with instruction for use of each formulation, including how to prepare each dose if required, how to administer each dosage and when to administer each dosage.

EXAMPLES

Figure 1A:
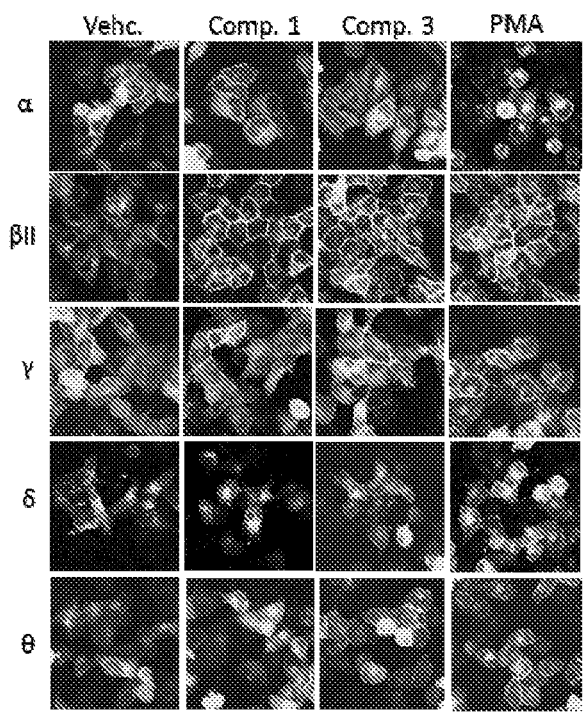
FIG. 1A provides: images of PKC-$\alpha$, -$\beta$II, -$\gamma$, -$\delta$ and -$\theta$ translocation after treatment with vehicle (Vehc.) or 500 nM Compound 1 (Comp 1), Compound 3 (Comp 3) and PMA. These images were also used for the quantitation shown in FIG. 1B.

The compounds of the present invention may be obtained by isolation from a plant or plant part, or by derivatisation of the isolated compound, or by derivatisation of a related compound. Isolation procedures and derivatisation procedures may be found in WO 2007/070985 and WO2014/169356.

Compound 6, the 20-acetyl derivative of compound 1 may be produced from Compound 1 by acetylation with acetic anhydride (1 equiv) in the presence of triethylamine in dichloromethane. These conditions allow selective acetylation of the C-20 hydroxy group without acetylation of the secondary hydroxy groups.

Compound 10, although not specifically synthesized in WO2014/169356, may be prepared using the general method for obtaining unsymmetrical esters set out in Example 1 of WO2014/169356, pages 64 to 70.

Example 1: Epoxytigliane Analogues Activate PKC Isoforms

Protein kinase C are a family of key enzymes involved in signalling pathways that specifically phosphorylate substrates at serine/threonine residues. Phosphorylation by PKC is important in regulation a variety of cellular events such as proliferation and regulation of gene expression. PKC isoforms (-θ, -η, -α, -β, -δ, -ε) are directly implicated in immune cell responses and can also promote the expression of key immune genes. However, the expression pattern and levels of each of these PKC isoforms are cell-type and context specific (Lim et al. 2015; Anel et al. 2012; Pfeifhofer et al. 2006).

To identify specific PKC isoform activation profiles (specificity and potency) of epoxytigliane compounds, HeLa cells were transiently transfected with a selection of PKC-EGFP vectors (PKC-α, PKC-βI, PKC-βII, PKC-γ, PKC-δ, PK-Cθ, PKC-η, PKC-ζ—generated in house) using Lipofectamine 2000 (Invitrogen) following methods described in Boyle et al. 2014. A volume corresponding to 0.16 µg PKC-EGFP and 0.48 µL Lipofectamine was mixed with 25 µl Opti-MEM medium (Invitrogen) and incubated for 5 min at RT. The solutions were combined and incubated for another 20 min at RT (1:3 ratio of DNA:Lipofectamine 2000). The complexes (50 µl) were added to each well and after 3 h incubation at 37° C., another 50 µl RPMI-1640, 10% FCS was added to a total volume of 100 µl per well. After 24 h incubation at 37° C., cells were washed with phosphate-buffered saline (PBS) and treated with 500, 50 and 5 nM of epoxytigliane. Three compounds could be tested per 96-well plate. Five 96-well plates were required per experimental run. After 1 h treatment, the cells were washed twice with 100 µl PBS and fixed with 50 µl of 2% formaldehyde/0.2% gluteraldehyde in PBS for 10 min. The fixed cells were subsequently washed twice with 100 μl PBS. To stain nuclei, Hoechst 3342 was used at a 1:10000 dilution. After 7 min of incubation in the dark, Hoechst was removed and cells were washed with PBS. Finally the cells were overlaid with 100 μl PBS and stored at 4° C. in the dark until imaging. Imaging was performed using a GE InCell Analyzer 2000. The translocation of PKC to plasma membrane or other subcellular positions was counted manually using Adobe Photoshop CS6.

The images showing translocation of selected PKC isoforms-α, -βII, -γ, -δ and -θ to the cell membrane in the presence of the epoxytigliane compounds Compound 1, Compound 3 as well as PMA (phorbol-12-myristate-13-acetate) are shown in FIG. 1A. These images indicate that different epoxytigliane compounds can activate different PKC isoforms.

Figure 1B:
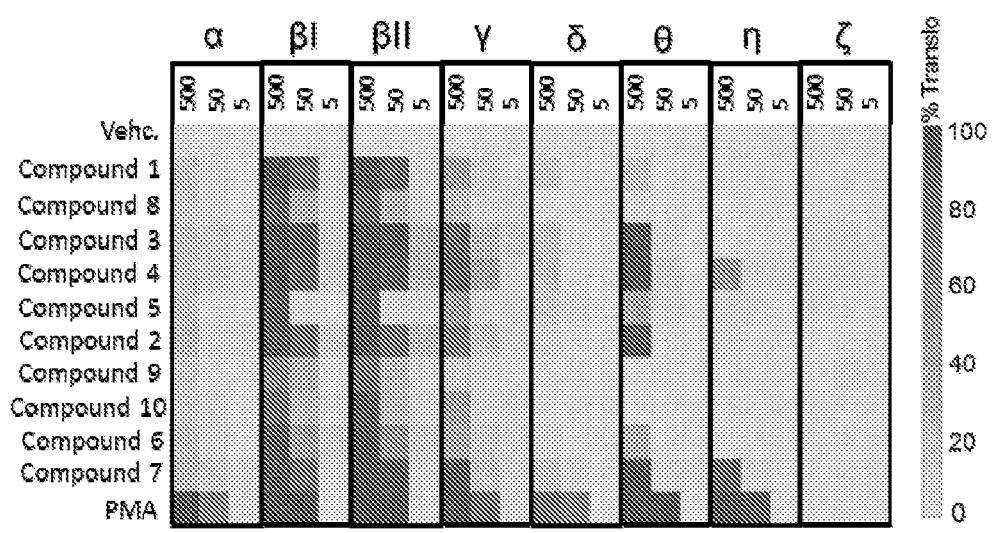
FIG. 1B: Heatmap depicting PKC isoform translocation profile (-$\alpha$, -$\beta$I, $\beta$II, -$\gamma$, -$\delta$, -$\theta$, -$\eta$ and mean -$\zeta$—of cells showing EGFP translocation to the plasma membrane) in response to 500, 50 and 5 nM Compound 1 and the indicated analogues. >150 cells counted per biological replicate. n=3.

The percentage of cells showing plasma membrane translocation of Compounds 1 to 10 as well as positive control PMA were converted to a Heatmap depicting the PKC isoform translocation profile in response to 500, 50 and 5 nM of each compound. The Heatmap is shown in FIG. 1B.

The results show that Compounds 1 to 7 all activate PKC-θ (to differing extents), a PKC isoform known to be involved in T- and NK-cell activation and the suppression of Treg development (Brezar et al., 2015; Anel et al., 2012). All epoxy-tigliane compounds activate PKC-β, which is critical in B cell receptor signalling and antigen presentation (e.g. Kang et al. 2001; Lim et al. 2015). Three other PKC isoforms (-η, -α, -δ) which were more weakly activated by some or all of the epoxytiglianes have also been directly implicated in immune cell responses (Lim et al. 2015; Pfeifhofer et al. 2006)

Example 2: Gene Expression Changes in Mouse Tumour Stroma Consistent with Immune Cell Recruitment and the Induction of a Th-1/M1-Like Anti-Tumour Immune Response The Th1/M-1 Like Response in Anti-Tumour Immunity.

A Th1/M1-like immune response has been associated with induction of anti-tumour cellular immunity through a range of mechanisms including direct tumouricidal activity, modification of anti-tumour cytokine responses and potentiation of long-term immunologic memory. For example, several lines of evidence show that $CD4^+$ T helper type 1 (Th1) cells, the drivers of Th1 immunity, can help support the clearance of tumour cells via the secretion of various cytokines, including interferon-γ (IFN-γ), interleukin-2 (IL-2), and tumor necrosis factor-α (TNF-α) (Knutson et al. 2005; DeNardo et al. 2010; Burkholder et al. 2014). These cytokines promote the activities of several cell types, including antigen presenting cells (APCs), cytotoxic T cells, NK cells, and various innate immune cell subtypes (e.g. Cohen et al. 2000; Bos & Sherman 2010). IFN-γ and TNF are also known to have direct effects on tumour cell survival (Sugarman et al. 1985; Bayaert et al. 1994). Although IL-1 and IL-6 (produced by M1 macrophages) have been associated with tumour development, more recent evidence suggests that they are in fact crucial components of acute anti-tumour immune responses (Haabeth et al. 2011; Gabrilovich et al. 2012; Haabeth et al. 2016). They have been shown to enhance B cell proliferation and antibody production, increase the activity of antigen-presentation cells (APC), stimulate the proliferation of antigen specific cytotoxic cell types and promote Th1 cell differentiation (Haabeth et al. 2011; Burkholder et al. 2014). Combinations between Th1 and M1 cytokines have also been shown to be important in tumour immunosurveillance. For example, both IL-1 and IFN-γ synergise to activate the tumouricidal activity of macrophages (Hori et al. 1989; Haabeth et al. 2016). Importantly, the occurrence of M1 macrophages and Th1 lymphocytes in tumours has been positively associated with improved prognosis and survival times in many cancers (Pages et al. 2010; Fridman et al. 2012; Senovilla et al. 2012). Indeed, inducing Th1/M1-type inflammation has been proposed to significantly improve anti-cancer immunotherapy based approaches (Haabeth et al. 2012). Below the effect of Compound 1 in promoting a Th1/M1 like anti-tumour immune response in the stroma of a xenograft mouse model is described.

Mouse Stroma in Human Tumour Xenografts from Mice.

The SK-MEL-28 human melanoma cell line was injected subcutaneously (s.c) into 2 sites on the flanks of each BALB/c Foxn1nu mouse (2 million cells/site) and allowed to grow to approximately 7 mm diameter. Each tumour was then injected with 50 μl of 20% propylene glycol containing 30 μg Compound 1 or with 50 μl of 20% propylene glycol. At different times after injection a mouse was euthanased and the tumours harvested, the skin covering removed, and the intact tumours stored at −80° C.

RNA Extraction.

RNA was extracted from 30 mg of frozen tumour using the Qiagen RNeasy Plus Mini Kit, according to manufacturer's instructions, then quantitated with a NanoDrop instrument and integrity confirmed on denaturing agarose gels bearing a 1 kb DNA marker and stained with ethidium bromide.

RNA Amplification and Labelling.

Approximately 500 ng of total unlabelled RNA was adjusted to a final volume of 11 μl with nuclease-free water. The RNA was incubated with 9 μl of the reverse transcriptase master mix (1 μl of T7 Oligo (dT) Primer, 2 μl of 10× first strand buffer, 4 μl of dNTP mix, 1 μl of RNase inhibitor and 1 μl of ArrayScript) at 42° C. for 2 h. This was followed by the second strand cDNA synthesis step which involved a further incubation at 16° C. for 2 hr with 80 μl of the second strand master mix (63 μL nuclease-free water, 10 μl 10× second strand buffer, 4 μl dNTP mix, 2 μl DNA polymerase and 1 μl RNase H). The cDNA was purified by filtering through a cDNA Filter Cartridge with 250 μl of cDNA binding buffer and washing with 500 μl of the wash buffer provided in the kit. Purified cDNA was eluted with 20 μl of 55° C. nuclease-free water. Each cDNA sample was incubated with 7.5 μl of the IVT master mix (2.5 μl of T7 10× reaction buffer, 2.5 μl of T7 enzyme mix and 2.5 μl biotin-NTP mix) at 37° C. for 16 h. The reaction was stopped with the addition of 75 μl of nuclease-free water to each cRNA sample. The biotinylated, amplified RNA was purified by filtering the cRNA samples through cRNA Filter Cartridges with 350 μL of cRNA binding buffer and 250 μl of 100% ethanol mixed together prior to loading onto the filters. The cRNA filter cartridges with attached RNA were then washed with 650 μl of wash buffer before eluting purified cRNA with 200 μl of 55° C. nuclease-free water.

Illumina Expression BeadChip Hybridization.

The cRNA samples were heated at 65° C. for 5 min and collected by pulse centrifugation. After heating at 65° C. for 5 min, approximately 750 ng of the cRNA sample was aliquoted into separate tubes to which were added ~5 μl of RNase-free water and 10 μl of Hyb Mix. Approximately 15 μl of the prepared cRNA mix was loaded onto the Illumina Expression BeadChips. Subsequent steps of hybridisation and washing were carried out according to the Whole- Genome Gene Expression Direct Hybridization Assay Guide supplied by Illumina. The HumanHT-12 v4 Expression BeadChips cover more than 47,000 transcripts and known splice variants across the human transcriptome. The MouseRef-8 v2.0 Expression BeadChips cover approximately 25,600 well-annotated RefSeq (Reference Sequence) transcripts, comprising over 19,000 unique genes.

Data Analysis.

BeadChips were read by the iScan System, and transferred via GenomeStudio into GeneSpring GX v12.5 (Agilent Technologies, Santa Clara, Calif., USA). The expression values were normalized using quantile normalization with default settings. The entities were filtered based on the detection score calculated by GenomeStudio where p≤0.05 was considered significant.

Figure 2A:
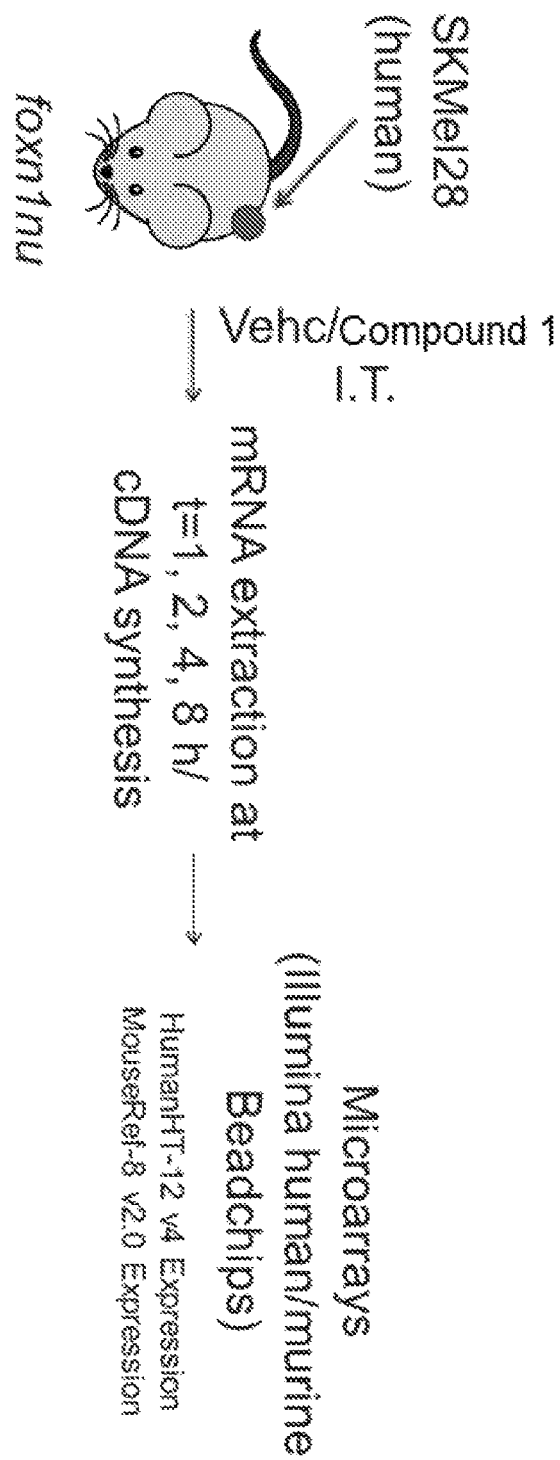
FIG. 2A provides: Schematic of the experimental design.
Figure 2B:
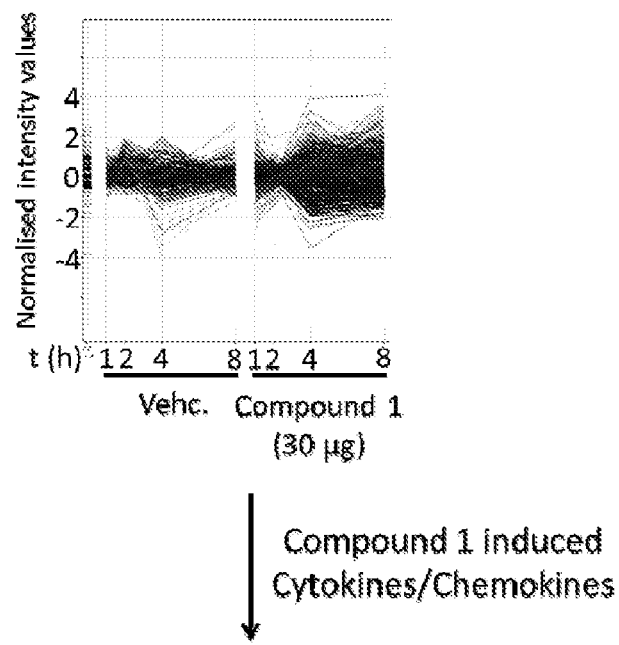
FIG. 2B: Select host cytokines/chemokines with roles in leukocyte recruitment are induced by Compound 1 treatment (30 µg). Fold changes in gene expression of the indicated cytokines/chemokines are shown.
Figure 2C:
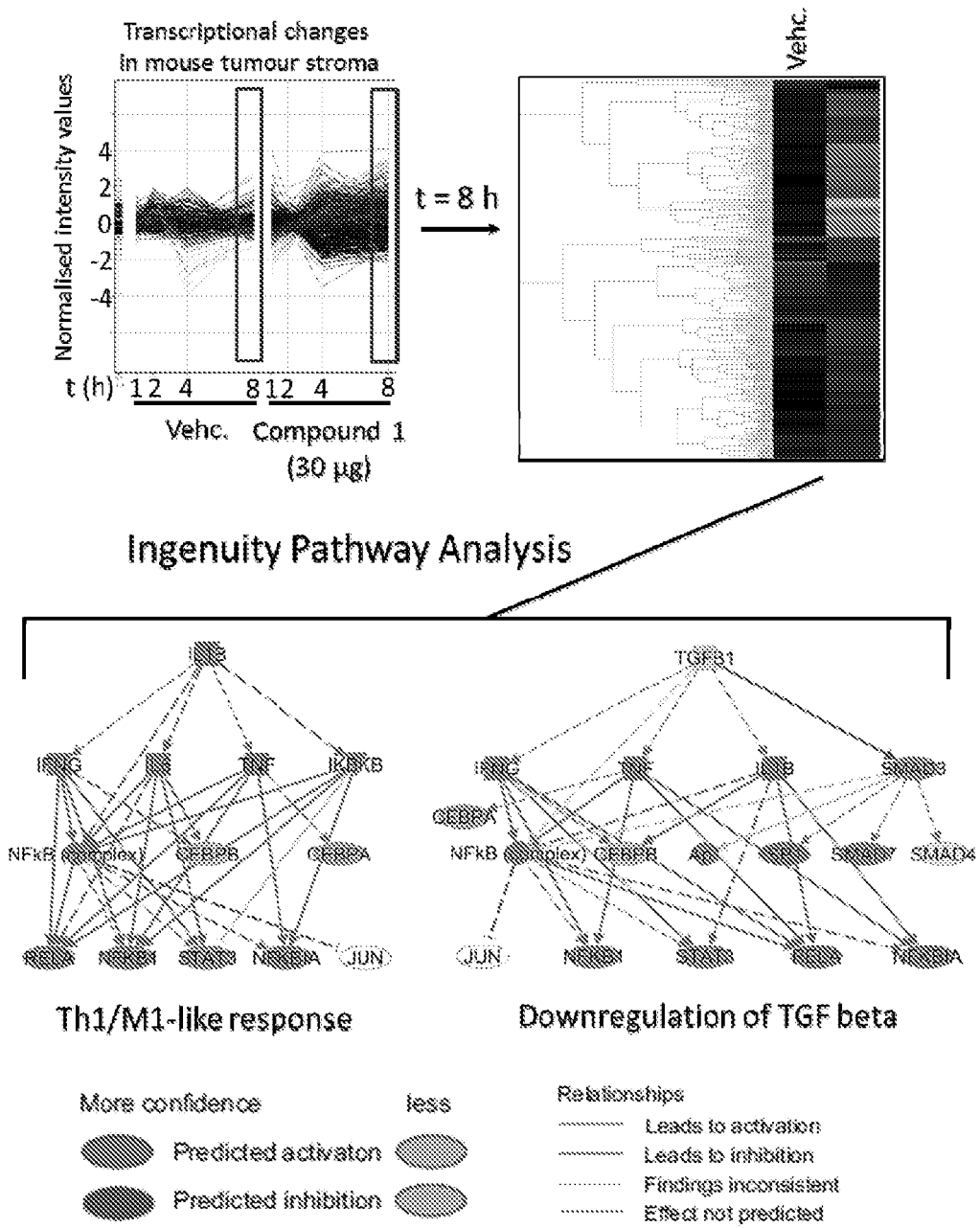
FIG. 2C: A heat map was generated after comparison of intensity data from both Vehicle and Compound 1 gene expression profiles at t=8 h. Subsequent gene lists were analysed by Ingenuity Pathway Analysis (IPA; Qiagen) to identify pathways affected by Compound 1 treatment.

The results are shown in FIG. 2. FIG. 2A shows that several host cytokines/chemokines which are important for the recruitment/activation of immune cells are upregulated at the tumour site in response to Compound 1 treatment. Of note, Cxcl1, which is heavily upregulated by Compound 1 is known to promote neutrophil recruitment and subsequent killing of residual cancer cells (Garg et al. 2017). Furthermore, FIG. 2B shows that Compound 1 induces gene expression changes in the host which are associated with the development of a Th-1/M-like response i.e. IFN-γ, TNF, IL-δ and IL-1β induction. The data also suggest that there may be a downregulation of TGF beta signalling (FIG. 2C), which is a known immunosuppressive signalling pathway (Neuzillet et al. 2015).

Example 3: Demonstration that Therapeutic Concentrations of Compound 1 and Other Epoxytiglianes Induce Cellular Oncosis Oncosis is a form of necrotic cell death, characterised by the swelling and rupture of subcellular organelles and subsequent permeabilisation of the plasma membrane, due in part to loss of ATP-driven ion pump activity that maintains osmotic balance. Oncosis has been shown to be immunogenic in nature and is associated with the efficacy of some oncolytic viruses and small molecules developed as anti-cancer agents (e.g. Dyer et al. 2016).

Cell Lines, Reagents and Media.

A431 (human epidermoid carcinoma), MM649 (human melanoma), B16-OVA (B16-F10 mouse melanoma cell line stably transfected with chicken ovalbumin), MM415 (human melanoma) and FaDu (human hypopharyngeal carcinoma) cells were cultured in RPMI-1640, 10% FCS (complete medium) at 37° C., 5% $CO_2$ in a humidified incubator. All cell lines used in this study were confirmed as *mycoplasma* negative using MycoAlert (Lonza). STR profiling was also performed to confirm the identity of the human cell lines used.

IncuCyte Cytotoxicity Assays.

Four cancer cell lines (A431, MM649 (human melanoma), FaDu (HNSCC) and MM415 (human melanoma) were assessed for their response to epoxytigliane treatment. Cells were plated at a density of 10,000 cells per well (100 μl of complete media) into clear bottom black 96-well plates (Corning, #3603). Following 24 h incubation, the media within each well was aspirated and replaced with 50 μl of fresh media containing 1 μg/ml propidium iodide (PI). Stock solutions (20 mg/ml in ethanol) of four epoxytiglianes (Compounds 1, 2, 3 and 4) were diluted to 2× final assay concentration (1 mM) in identical media and inserted into a U-bottom 96 well plate in preparation for transfer. 50 μl of dilution was added to the required wells and the resultant plates inserted into an Essen Biosciences IncuCyte in preparation for imaging. Images were acquired at various time points (30 min, 1 h and at hourly intervals) for a total of 24 h.

Lactate Dehydrogenase (LDH) Release Assays.

Measuring the release of LDH is a well-recognised assay to assess plasma membrane permeabilisation and detect cell death by necrosis (Chan et al. 2013). Three cell lines (A431, MM649 and B16-OVA) were used in these assays. Cells were plated at a density of 10,000 cells per well into clear 96-well plates (Corning, #3595; 100 μl of complete media) and the resultant plates incubated overnight as previously detailed. The following day, media was aspirated from each well and 50 μl of fresh medium was inserted. Stock solutions of Compound 1 were diluted to 2× final assay concentrations (1 mM and 600 μM) and 50 μl of these dilutions added to the required wells. Ethanol only control solutions were also compiled and administered. At the indicated time points, 50 μl of media was removed and assayed for LDH release using a Pierce LDH cytotoxicity assay kit (ThermoFisher Scientific). OD490 nm and OD690 nm readings were recorded for each sample using a Hybrid Synergy H4 plate reader. Absorbance readings from drug treated samples were normalized to detergent treated controls to determine the % LDH release per well.

Intracellular ATP Assay.

CellTiter-Glo® 2.0 assay kits (Promega Corporation), a luminescence based assay quantitating the amount of ATP present in cells, were used to determine intracellular ATP levels in cultures of A431 and MM649 exposed to two concentrations (300 μM and 500 μM) of Compound 1. Again, cells were plated at a density of 10,000 cells per well into a clear bottomed black 96-well plates (in 100 μl of complete medium) and incubated at 37° C., 5% $CO_2$ overnight. At the time of assay, media was aspirated from each well and 50 μl of fresh medium was inserted. Stock solutions of Compound 1 were diluted to 2× final assay concentrations (1 mM and 600 μM) and 50 μl of these dilutions added to the required wells. Ethanol only control solutions were also compiled and administered. At the indicated time points, media was gently removed making sure not to disturb the cells and 100 μl of CellTiter-Glo® 2.0 Reagent added. The resultant plate was mixed on an orbital shaker for 2 mins to induce cell lysis after which it was incubated in the dark for 10 mins. Following this, the luminescent signal in each well was determined. Luminescent signals from compound treated wells were normalised to Vehicle treated wells and expressed as % intracellular ATP vs. time.

Images acquired from the IncuCyte showed strong red staining after 120 minutes in the majority of cells of all four cell lines treated with 500 μM of Compound 1, 2, 3 and 4 (A431, FaDu, MM649 and MM415). There was no staining of cells treated with the vehicle only, confirming loss of plasma membrane integrity was confined to cells treated with Compound 1. In addition, significant cytoplasmic swelling and 'blistering' was also observed in all cells treated with Compound 1, 2, 3 and 4, although to differing extents and with different kinetics of onset.

Figure 3A:
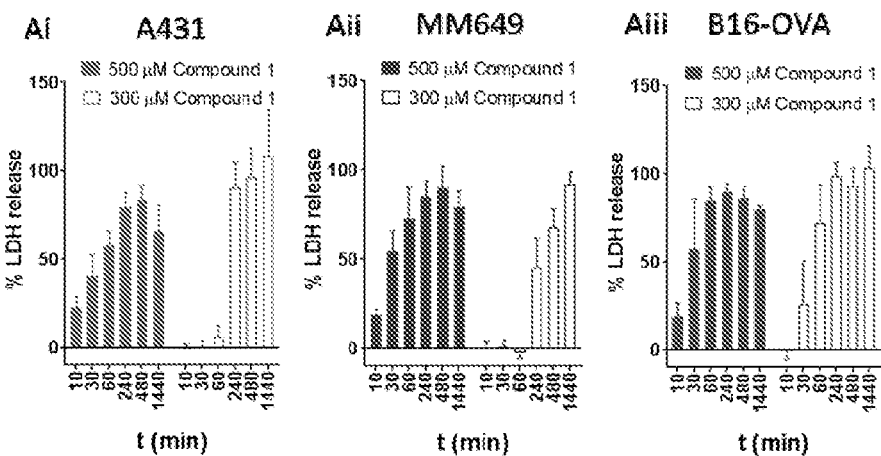
FIG. 3A provides: LDH release from cancer cell lines treated with Compound 1. A431, MM649 and B16-OVA were treated with Compound 1 at the indicated concentrations or vehicle only (Vehc.) and LDH released assayed over time using a Pierce LDH cytotoxicity assay kit. n=3.
Figure 3B:
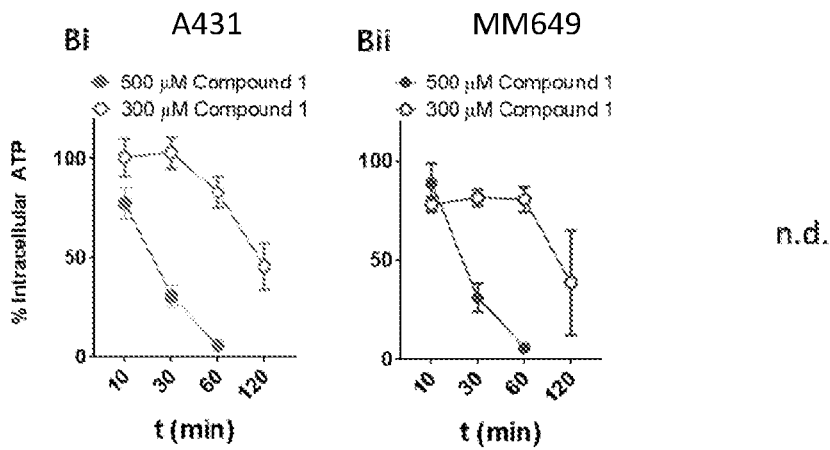
FIG. 3B: Compound 1 induces significant reduction of intracellular ATP levels. Again, cells were treated with Compound 1 or Vehicle (Vehc.) and intracellular ATP levels were assayed at the indicated timepoints using a CellTiter-Glo 2® assay kit. n=3.

Results from assays for assessing the release of LDH and for evaluating intracellular ATP levels are shown in FIGS. 3A and 3B, respectively. Compared to the controls, there was significant release of LDH from all three cancer cell lines treated at both concentrations of Compound 1 that were tested (300 μM and 500 μM) (FIG. 3A). Intracellular ATP levels declined very rapidly following treatment with 500 μM of Compound 1 and were almost undetectable after 60 minutes (FIG. 3B). At 300 μM of Compound 1, intracellular ATP declined more slowly, and less catastrophically, than for the 500 µM concentration of Compound 1, being approximately 50% of the pre-treatment level after 120 minutes (FIG. 3B). ATP depletion has been previously associated with the induction of oncosis (Kim et al. 2003).

These results demonstrate that the epoxytigliane compounds induce oncosis at therapeutically relevant concentrations (i.e. those concentrations which are effective in inducing haemorrhagic necrosis in vivo).

Example 4: The Oncosis Induced by Compound 1 and Other Epoxytiglianes Displays Characteristics of Immunogenic Cell Death Immunogenic cell death (ICD) is a specific type of regulated cell death which results in the release or externalisation of mediators called damage associated molecular patterns (DAMPs), which interact with receptors expressed by dendritic cells/macrophages to promote their recruitment and stimulate the uptake/presentation of tumour antigens to T cells. ICD is a prominent pathway for the activation of the immune system against cancer. Biochemical hallmarks of ICD include the exposure of calreticulin (CALR) and other endoplasmic reticulum/mitochondrial proteins on the surface of dying cells, and the release of large amounts of ATP and high-mobility group box 1 (HMGB1) into the extracellular environment (Kroemer et al. 2013). These parameters have been used to make accurate predictions about the capacity of chemotherapeutic drugs (including doxorubicin, mitoxantrone, oxaliplatin and bortezomib) to induce ICD (Kroemer et al. 2013; Galluzzi et al. 2017). The ability of the epoxytiglianes to induce these characteristics is detailed below.

Cell Lines, Reagents and Media.

A431 (human epidermoid carcinoma), MM649 (human melanoma) and B16-OVA (B16-F10 mouse melanoma cell line stably transfected with chicken ovalbumin) were cultured in RPMI-1640, 10% FCS (complete medium) at 37° C., 5% $CO_2$ in a humidified incubator. BMDCs were cultured in R10 media (RPMI, 10% FCS, 2 mM glutamine, 50 µM beta-mercaptoethanol, Pen/Strep). All cell lines used in this study were confirmed as *mycoplasma* negative using MycoAlert (Lonza). STR profiling was also performed to confirm the identity of the human cell lines used.

ATP Release Assays.

Cell lines were plated at a density of 10,000 cells per well into clear 96-well plates (Corning, #3595; 100 µl of complete media) and the resultant plates incubated overnight as previously detailed. The following day, media was aspirated from each well and 50 µl of fresh medium was inserted. Stock solutions of Compounds 1, 2, 3 and 4 were diluted to 2× final assay concentration (1 mM and 600 µM) and 50 µl of these dilutions added to the required wells. Ethanol only control solutions were also compiled and administered. At the indicated timepoints, 80 µl of media was removed, centrifuged at 1,200 rpm for 4 mins to pellet cell debris and 50 µl assayed for ATP using a bioluminescence based ATP assay kit (FLAA, Sigma-Aldrich). Relative luminescence units were recorded for each sample using a Hybrid Synergy H4 plate reader (BioTek).

HMGB1 Release Assays.

Cell lines (A431, MM649 and B16-OVA) were plated into T75 $cm^2$ flasks (Nunc) in 10 ml of complete media and cultured at 37° C., 5% $CO_2$ until they reached 90% confluency. Compounds 1, 2, 3 and 4 were diluted in 5 ml of identical media to a final concentration of 500 and 300 µM and then administered to the cells. Several flasks were prepared such that a kinetic curve of HMGB1 release in response to drug treatment could be established. Ethanol only controls were also generated. At the required timepoint, media was removed from the flask into a 10 ml polypropylene tube that was placed on ice for 5 mins. Cell culture supernatants were centrifuged at 1,200 rpm for 4 mins to remove cellular debris, after which 4.5 ml of supernatant was inserted into a concentrator spin column (Amicon® Ultra 50 kDa cut-off membrane, Merck) to remove FCS. The flow through from this column was then inserted into another concentrator column (Amicon® Ultra 10 kDa cut-off membrane, Merck) and centrifuged at 3,500 rpm to concentrate HMGB1 prior to assay via ELISA (SEA399Hu/SEA399Mu, Cloud-Clone Corp). OD450 nm values were determined using a Hybrid Synergy H4 plate reader (BioTek). Absorbance values from drug treated samples were normalized to vehicle treated samples to determine the fold increase in HMGB1 release in response to epoxytigliane treatment.

Calreticulin Externalization Assays.

Calreticulin externalization was determined as previously detailed (Gomez-Cadena et al. 2016). Briefly, cells (A431, MM649, B16-OVA) cultured in complete medium at 37° C., 5% $CO_2$ were detached via trypsinisation, centrifuged at 1,200 rpm and washed ×2 with fresh medium. After an additional round of centrifugation, the resultant cell pellet was resuspended at a concentration of $1 \times 10^6$ cells/ml, after which epoxytigliane was added to a final concentration of 500 or 300 µM. Ethanol only controls were also performed. Cell suspensions were incubated at 37° C., 5% $CO_2$ and at the indicated timepoints, 200 µl of sample was removed and incubated with LIVE/DEAD fixable far red stain for 5 mins on ice. Following this, cells were pelleted at 1,200 rpm for 4 mins and washed ×1 with PBS. 500 µl of PBS, 0.25% formaldehyde was then added to each pellet to perform a light fixation without compromising plasma membrane integrity. Following this, the cells were washed ×1 with PBS and 100 µl of PBS, 1% BSA, 2 mM EDTA (FACs buffer) containing anti-Calreticulin (ab2907, Abcam; 1:50 dilution) added. After 1 h incubation at room temperature, cells were centrifuged at 1,200 rpm for 4 mins and washed ×1 with FACs buffer prior to incubation with 100 µl of FACs buffer containing anti-rabbit Alexa488 at 1:750 for a further hour at room temperature. Cells were again pelleted and then resuspended in 500 µl of FACs buffer in preparation for flow cytometry.

Samples were gated by FSC-H v FSC-A first to identify single cells, after which the LIVE/DEAD stain (Ex: 640 nm, Em: 670/14) negative (intact cell) population was analysed for green fluorescence (Ex: 488 nm, Em: 530/30; calreticulin externalization). Mean fluorescence intensity values were subsequently determined and graphed versus time.

Figure 4A:
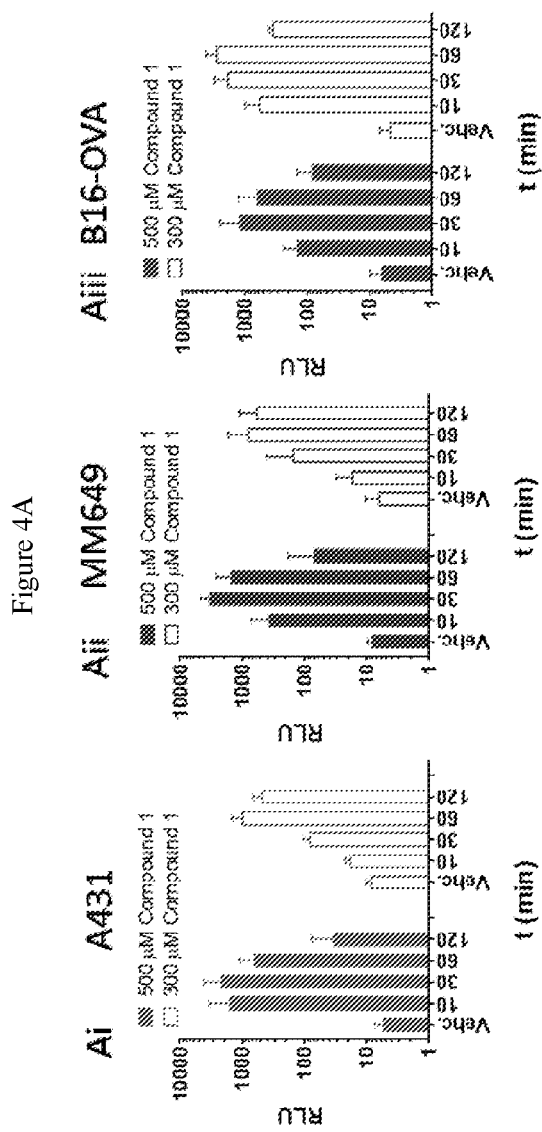
FIG. 4A provides: Determination of ATP release from cancer cell lines in response to treatment with Compound 1. Cells were treated with Compound 1 or Vehicle (Vehc.) for the indicated times and ATP release from cell culture supernatants was assayed using a bioluminecsence based ATP assay kit. Mean RLU values+/−S.D. were determined and plotted vs. time. n=4.
Figure 4B:
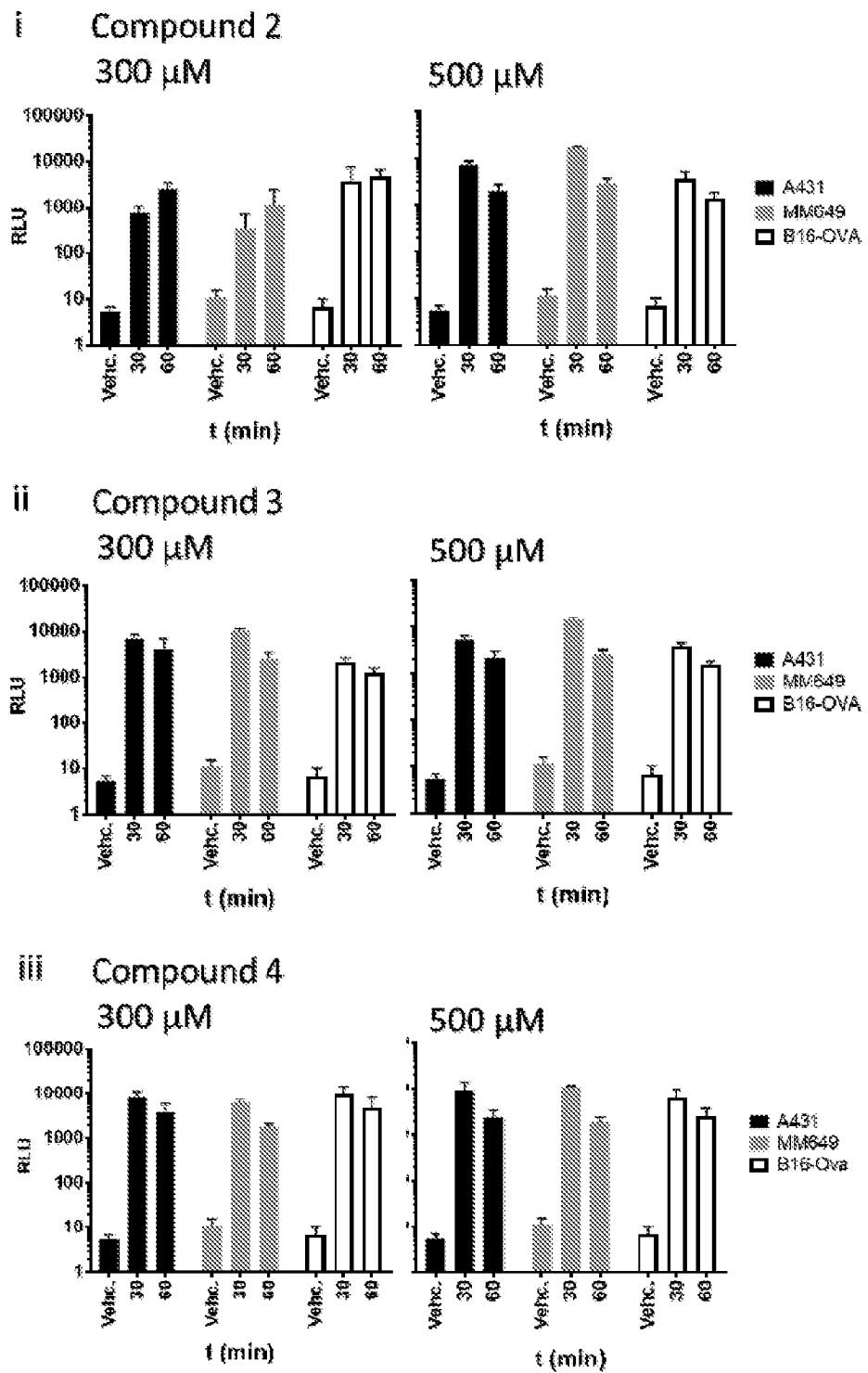
FIG. 4B: Additional epoxytigliane analogues (Compound 2: Bi, Compound 3: Bii, and Compound 4: Biii) also promote ATP release from A431, MM649 and B16-OVA cell lines. n=4.
Figure 4C:
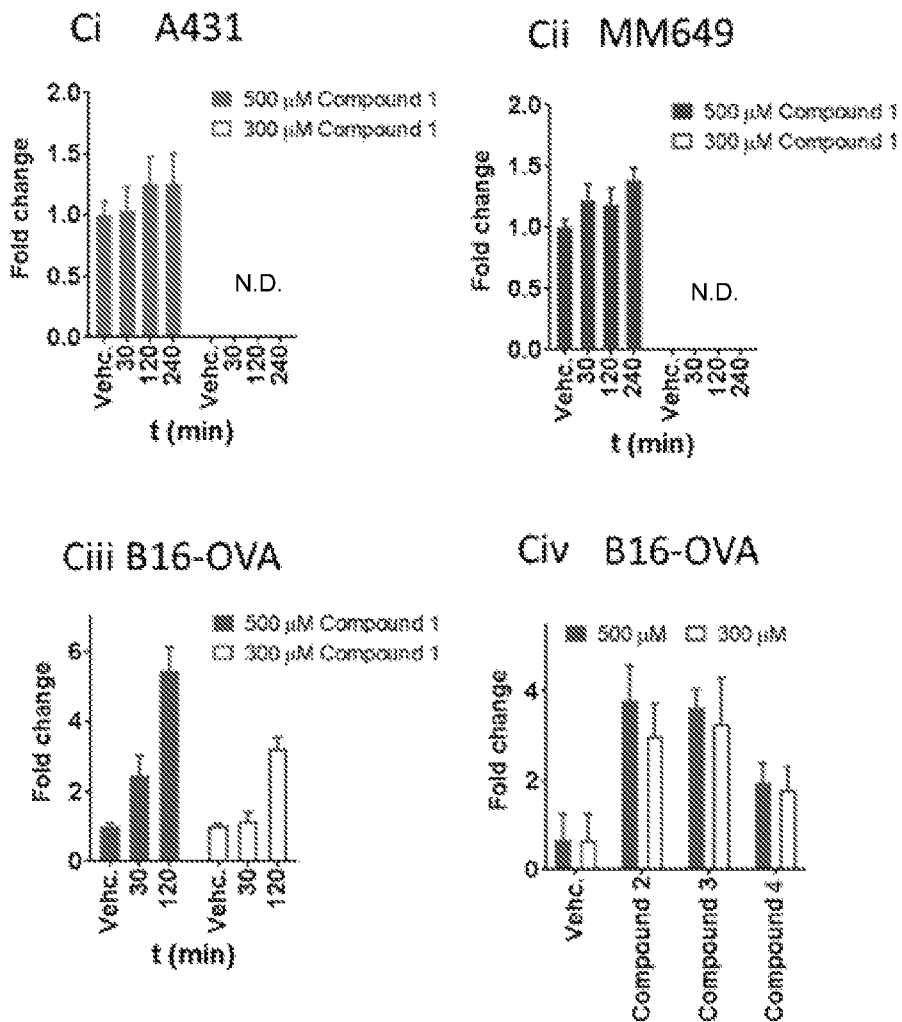
FIG. 4C: Determination of HMGB1 release from cancer cell lines treated with the Compound 1 and epoxytigliane analogues. Cell culture supernatants from epoxytigliane or vehicle (Vehc.) treated A431 (Ci), MM649 (Cii) or B16-OVA (Ciii) were analysed for HMGB1 release via ELISA. Values from Compound 1 treated cells were normalised to vehicle treated cells to determine fold increase in HMGB1 release. n=2 for A431 and MM649, whilst n=3 for B16-OVA. (Civ) HMGB1 release also occurred in response to treatment with Compound 2, 3 and 4. n=3.
Figure 4D:
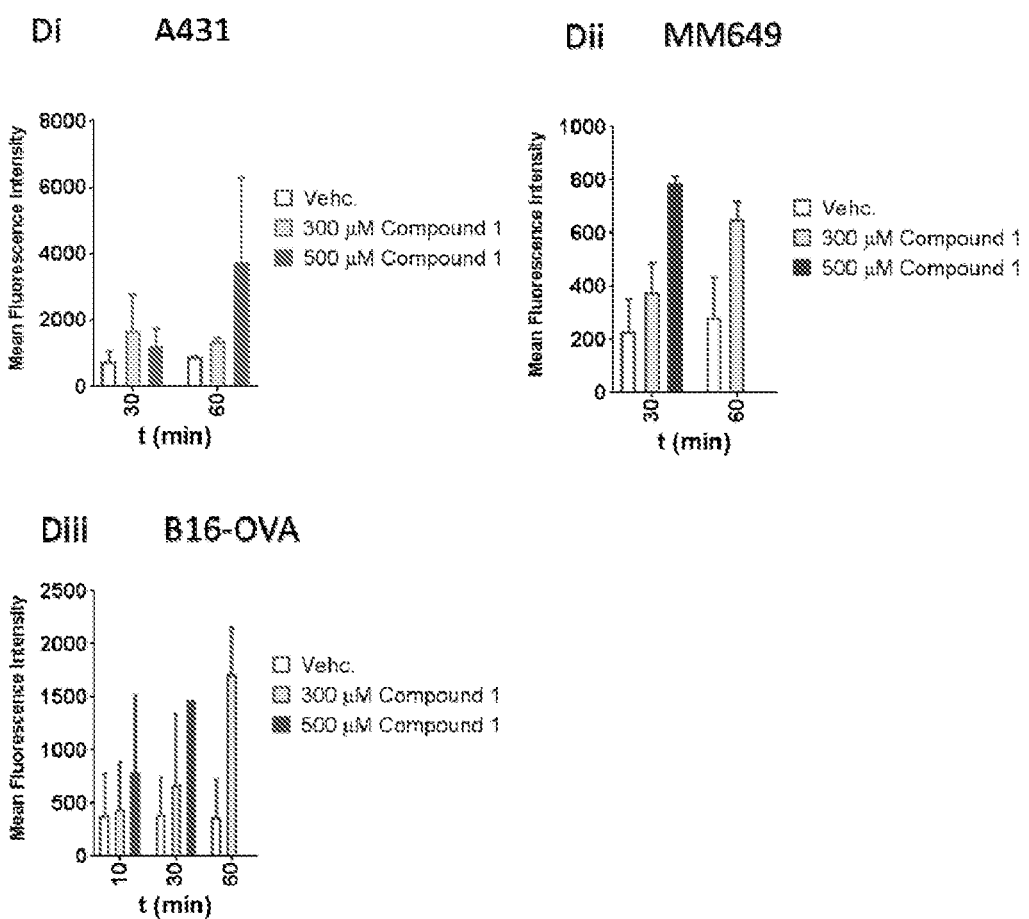
FIG. 4D: Compound 1 promotes calreticulin externalisation in a range of cancer cell lines. A431 (Di), MM649 (Dii) and B16-OVA (Diii) were treated with Compound 1 or Vehicle (Vehc.) only for the indicated times and then stained with anti-Calreticulin/anti-rabbit Alexa 488 prior to flow cytometry. Mean fluorescence intensity values (Ex:488 nm, Em: 530/530 nm)+/−S.D. are indicated for each timepoint.

The results showed that the rapid oncosis induced by epoxytigliane compounds also induced characteristics of immunogenic cell death, with the release/externalisation of critical DAMPs including ATP (FIGS. 4A and 4B), HMBG1 (FIG. 4C) and calreticulin (FIG. 4D). There was significant release of ATP within 60 minutes in all three cancer cell lines treated with both concentrations of Compound 1 (FIG. 4A) and of Compounds 2, 3 and 4 (FIG. 4B). These compounds also promoted release of HMGB1 from cancer cell lines. After ELISA assay values for treated cells were normalised to vehicle treated cells to determine fold increase, Compound 1 was shown to increase HMBG1 release within 120 minutes by up to 40% for A341 and MM649 cells (FIGS. 4Ci and 4Cii), and by greater than 3-fold for B16-OVA cells (FIG. 4Ciii). Compounds 2, 3 and 4 which were also assayed on B16-OVA cells and showed a minimum of 2-fold increase in HMBG1release from this cell line after 120 minutes (FIG. 4Civ). Data for calreticulin externalisation following treatment of the 3 cell-lines with Compound 1 showed significant increases in mean fluorescence intensity within 60 minutes of treatment (FIG. 4D). Such DAMP release/externalisation is known to promote the recruitment of antigen presenting cells, stimulate the efficient uptake of cancer cell associated antigens and stimulate presentation to T cell subsets (Kolaczkowska & Kubes, 2013)

Example 5: Fragments from Epoxytigliane Treated Cancer Cells are Ingested by CD11c$^+$ Bone Marrow Derived Cell Populations CD11c is a well described marker of DC/macrophages (Merad et al. 2013). One way to investigate the potential of anti-cancer agents (and the associated death processes they induce) to promote the development of immunogenic responses is to determine whether they lead to the uptake of cellular components by CD11c$^+$ dendritic cells/macrophages and their subsequent maturation into bone fide antigen presenting cells (APCs) (Guermonprez et al. 2002). Here we demonstrate that the oncosis induced by the Compound 1 and related epoxytiglianes leads to uptake of dying cancer cell components by such cells.

Isolation and Culture of Bone Marrow Derived Cell (BMDC).

The tibias and fibias from four 7-8 week old C57Bl/6 mice were first surgically removed under sterile conditions. The marrow was flushed from the bone cavity with 10 ml of ice cold R10 media (using a 27G needle/syringe into a 50 ml polypropylene tube). Cells were pelleted at 1,500 rpm for 5 mins and washed ×2 with ice cold R10 media. After resuspension of the pellet into 10 ml of ice cold R10 medium, cells were counted using an improved haemocytometer and plated at a density of 2×10$^6$ cells per plate (petri dish) in 10 ml of R10 supplemented with 20 ng/ml murine GM-CSF. All plates were incubated at 37° C., 5% $CO_2$ and at day 3 an additional 10 ml R10 with 20 ng/ml GM-CSF was added. Cells were again fed at day 6 and used for downstream assays on day 7.

BMDC Uptake Experiments.

Prior to co-incubation with BMDCs, B16-OVA cells were trypsinised, centrifuged at 1,200 rpm for 4 mins to pellet cells and washed ×2 with complete medium. Cells were then stained with 2 µM Cell Tracker Green in complete medium for 45 mins, after which they were pelleted and washed ×2 as above. Labelled B16-OVA cells were subsequently treated with Compounds 1, 2, 3 and 4 at two concentrations (500 or 300 µM) in media at a density of 1×10$^6$ cells/ml for 30 and 60 mins, after which cells were pelleted via centrifugation, supernatant removed via aspiration and the cell pellet washed ×1 with complete media. After the wash, the treated cells were resuspended in R10 media, inserted into the wells of a 6-well plate (Corning, #3471. Ultra low attachment surface) and BMDCs added. Co-cultures were incubated for 4 h after which cell suspensions were transferred to a microfuge tube and centrifuged at 1,500 rpm for 5 mins. Pellets were resuspended in 100 µl FACs buffer containing anti-CD11c-APC and incubated for 10 mins at 4° C. Cells were again pelleted, washed ×1 with FACs buffer and then fixed using PBS, 1% formaldehyde for 10 mins. After centrifugation and removal of the supernatant, cells were resuspended in 500 µl FACs buffer in preparation for flow cytometry.

Samples were first gated by FSC-H v FSC-A, then SSC-H v SS-A to identify single cells. The proportion of CD11c$^+$ cells (Ex: 640 nm, Em: 670/14) with CMFDA$_{mid}$ (Ex: 488 nm, Em: 530/30) were then determined for treated and untreated cells as a percentage of all CD11c$^+$ cells.

Figure 5A:
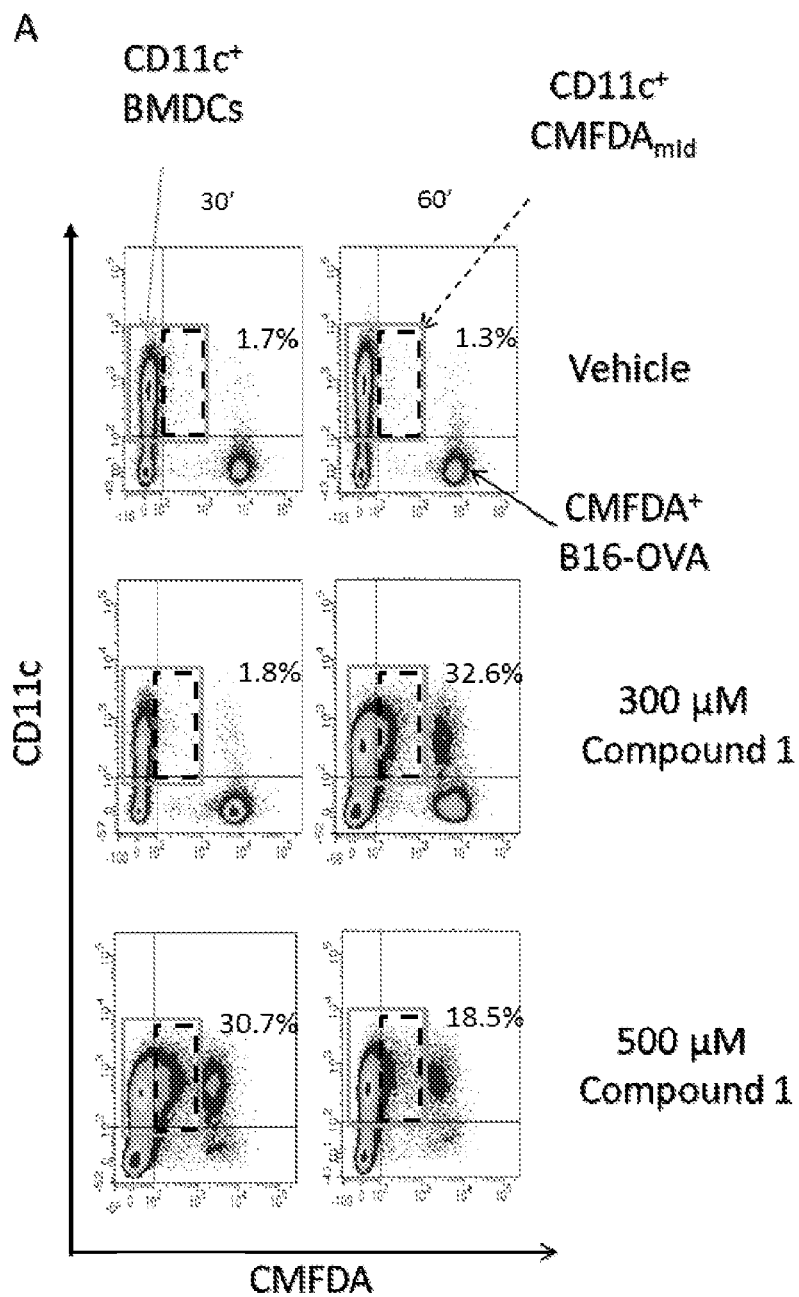
FIGS. 5A and 5B provide Epoxytigliane treated cells are processed by CD11c$^+$ BMDCs in vitro. CMFDA labelled B16-OVA cells treated with Compound 1 or vehicle (Vehc.) were incubated with immature BMDCs for 4 h and then stained with anti-CD11c-APC prior to flow cytometry. Solid grey box—CD11c$^+$ BMDC cells. Dashed black box—CD11c$^+$ BMDCs that have taken up dying B16-OVA cell fragments (CD11c$^+$ CMFDA$_{mid}$). The percentage of CD11c$^+$ CMFDA$_{mid}$ cells is indicated on FIG. 5A and data from 4 biological replicates is shown in FIG. 5B. n=4.
Figure 5B:
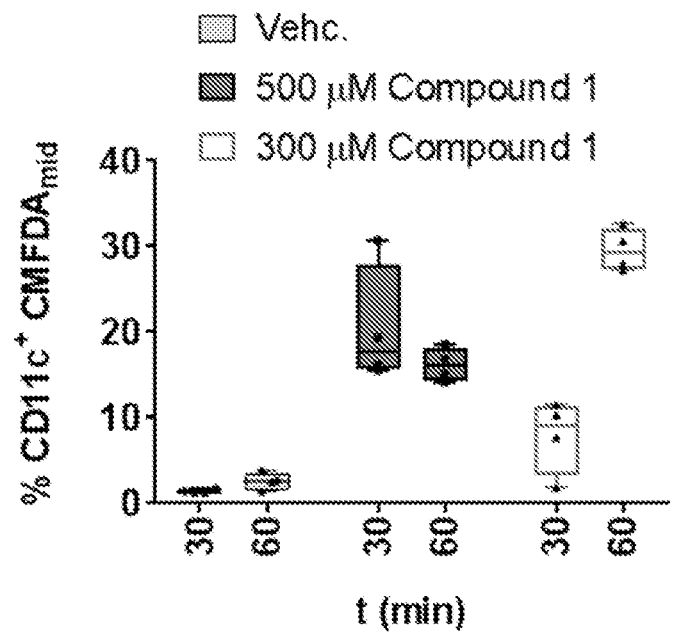
Figure 5C:
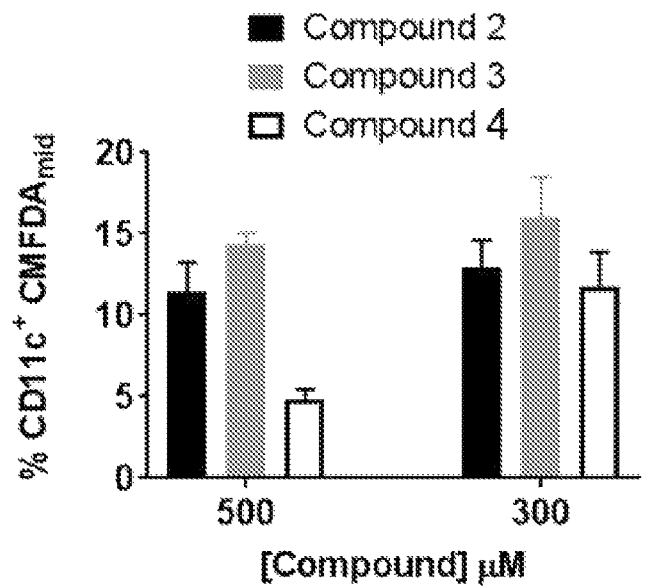
FIG. 5C provides Epoxytigliane analogues also induce uptake of B16-OVA cells by CD11c$^+$ BMDCs. Data acquired from the use of Compound 2, 3 and 4 are depicted. n=3.

The results (FIGS. 5A and 5B) show that the oncosis induced by Compound 1 promotes the uptake (i.e. effective ingestion) of dying cancer cell fragments by CD11c$^+$ dendritic cells/macrophages. This ingestion appears to be dependent on both Compound 1 concentration and treatment time, such that at 500 µM of Compound 1 antigen uptake occurs to a greater extent after a shorter treatment time compared to the use of 300 M. This is consistent with the kinetics of oncosis observed in Example 3. FIG. 5C demonstrates that Compounds 2, 3 and 4 are also capable of inducing a cell death response that is immunogenic in vitro i.e. promotes uptake by CD1c$^+$ BMDCs.

Example 6: Combination of Compound 1 with Immune Checkpoint Inhibitors

Immune checkpoint inhibitor therapies, especially those targeting receptors involved in T cell immunosuppression (e.g. cytotoxic T-lymphocyte-associated protein 4 (CTLA-4) or programmed death 1 (PD-1) and its ligand PD-L1), have greatly improved patient outcomes in several types of late stage cancer, including melanoma, renal cell carcinoma, bladder cancer and head and neck squamous cell carcinoma (HNSCC) (Msaouel & Massarelli 2016; Sharma & Allison 2015). However, primary and de novo resistance to these ICI drugs is a significant clinical problem. Furthermore, extensive clinical follow-up has shown that some melanoma patients are developing resistance to treatment and are undergoing disease relapse (O'Donnell et al., 2017). Therapies combining ICIs with compounds which may act as adjuvants by promoting immunogenic cell death (especially by resulting in increased immune cell infiltration into the tumour paracheyma and antigen uptake/presentation) hold promise to overcome some limitations of ICIs and improve overall clinical outcomes (Workenhe et al. 2014; Ribas et al. 2017). Here, and in Example 7, the data examines combinations of ICIs and intralesional injection of Compound 1.

Figure 6A:
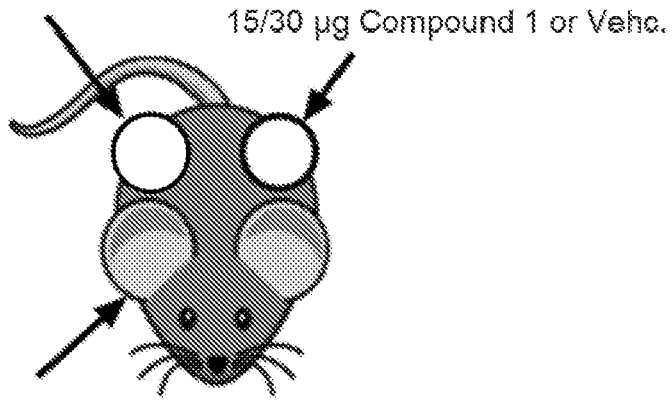
FIG. 6A provides: Schematic of the experimental approach to Compound 1 and ICI combinations. All tumours were injected with either 15/30 µg Compound 1 or Vehicle (Vehc.). Dosage regime of ICI treatment is also depicted.
Figure 6A:
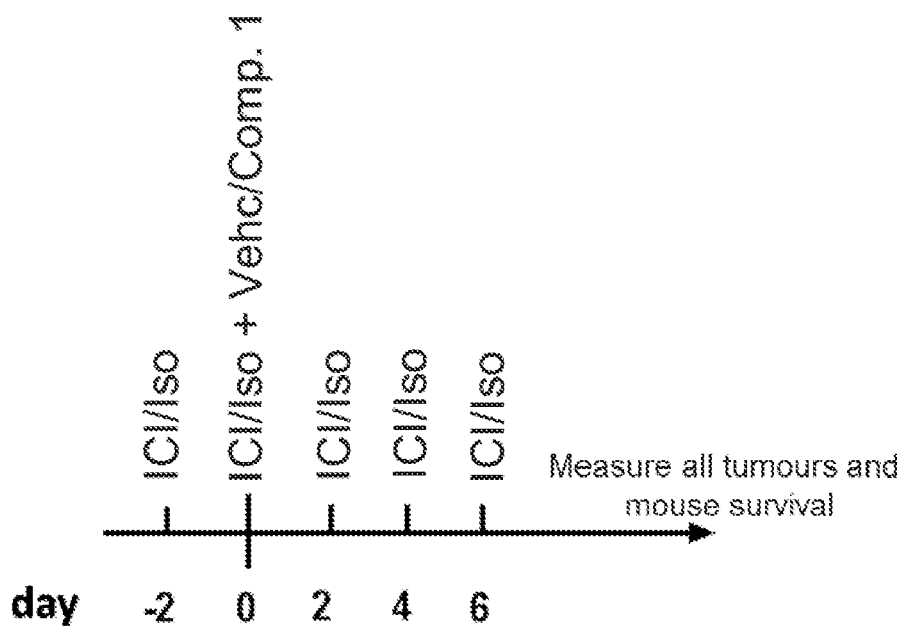

A schematic of the experimental approach can be seen in FIG. 6A. Briefly, 6-7 week old C57BL/6 mice were injected subcutaneously (s.c.) on both flanks with B16-F10-OVA mouse melanoma cells (2×10$^5$ cells per site in 100 µl). Tumours were allowed to develop to approximately 5-50 mm$^3$, after which 200 µg of anti-PD-1 (RMPI-14, BioXCell), anti-CTLA-4 (9H10, BioXCell) or isotype control antibody (2A3 and Syrian Hamster IgG, BioXCell) was injected i.p. per mouse (day −2). On day 0, both tumours were injected I.T. with either Compound 1 (15 µg in 50 µL) or vehicle (Vehc.) only. Each mouse received an additional i.p. injection of the same antibody that was administered on day −2 (again, 200 µg). Antibody was administered for a further 3 times via i.p. injection every 2 days. The volume of treated tumours was measured using calipers as previously detailed (Boyle et al. 2014) and mouse survival was determined over time.

Figure 6B:
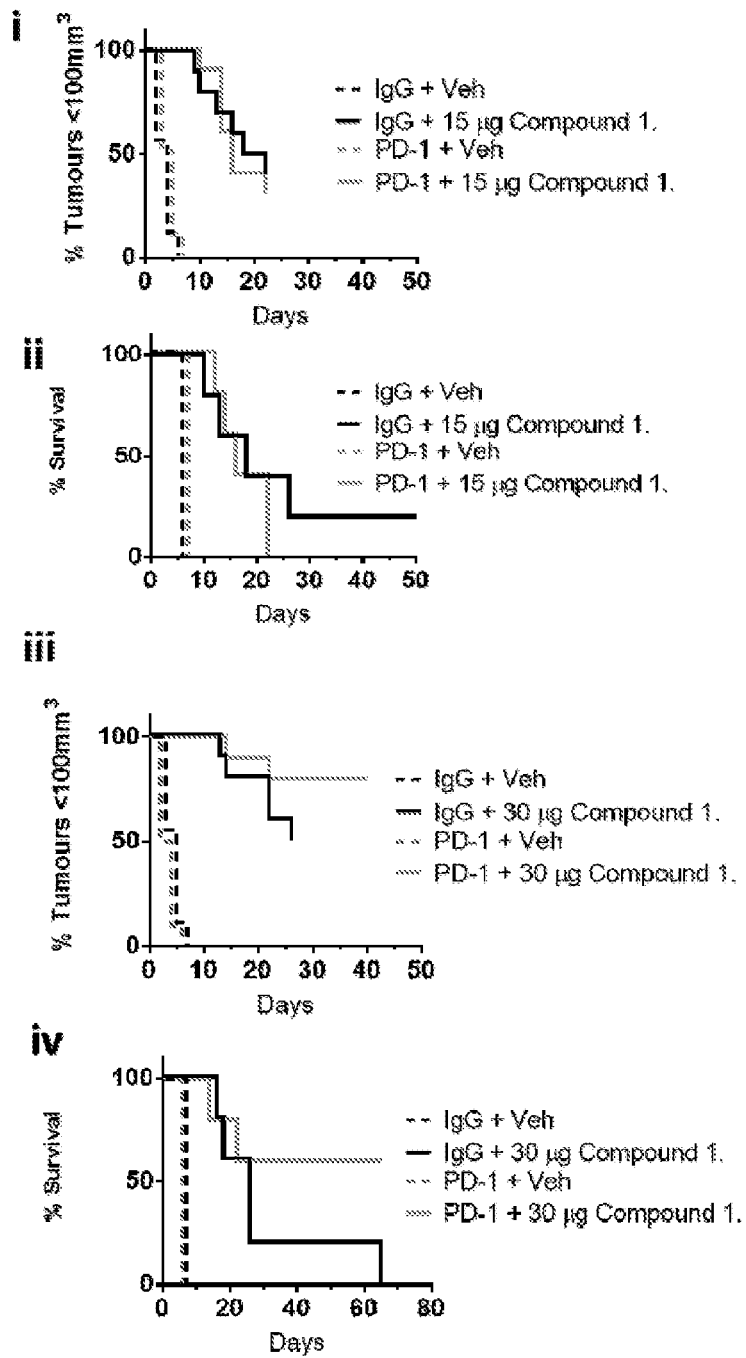
FIGS. 6B and 6C: Kaplan-Meier plots indicating the % of tumours treated that remain below 100 mm$^3$ in size under the distinct treatment conditions with ICIs, with either anti-PD-1 (FIG. 6B) or anti-CTLA-4 (FIG. 6C). Mouse survival in response to the combination is also depicted.
Figure 6C:
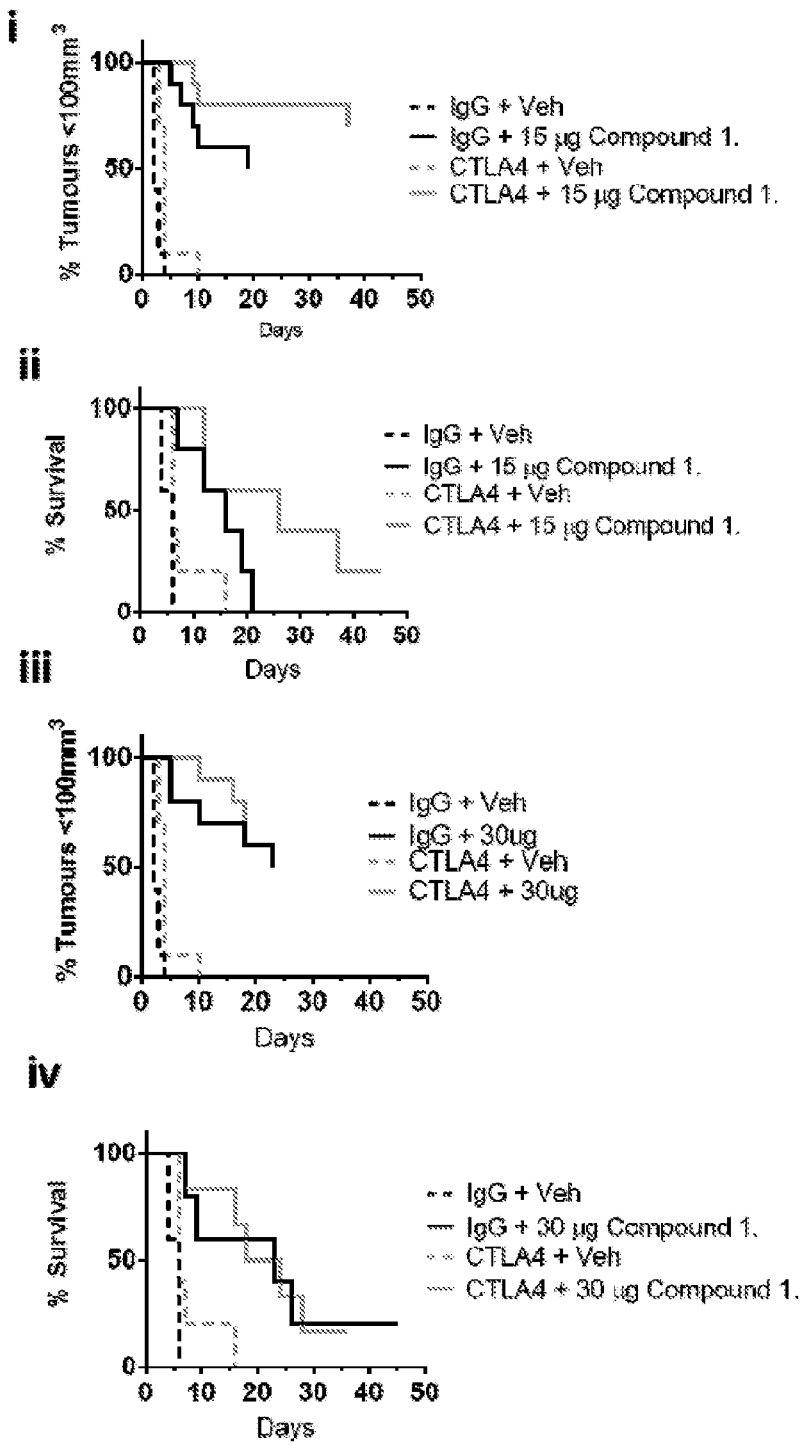

The results displayed in FIGS. 6B and 6C show that Compound 1 can combine with anti-PD-1 and anti-CTLA-4 to restrict tumour growth and improve mouse survival to a greater extent than single agent treatment. This effect appears to be concentration dependent for each Compound1/ICI combination. For example, the injection of 30 µg of Compound 1 together with anti-PD-1 leads to improved survival/reduced tumour growth when compared to the use of 30 µg of Compound 1 alone (FIG. 6Biii, iv). This is not observed when 15 µg of Compound 1 is used in the same combinations i.e. no improvement in survival or tumour growth (FIG. 6Bi, ii). The situation is reversed when anti-CTLA4 is used, where 15 µg of Compound 1 in the combination treatment (FIG. 6Ci, ii) gives the optimal response and 30 µg of Compound 1 does not (FIG. 6Ciii, iv).

Figure 7A:
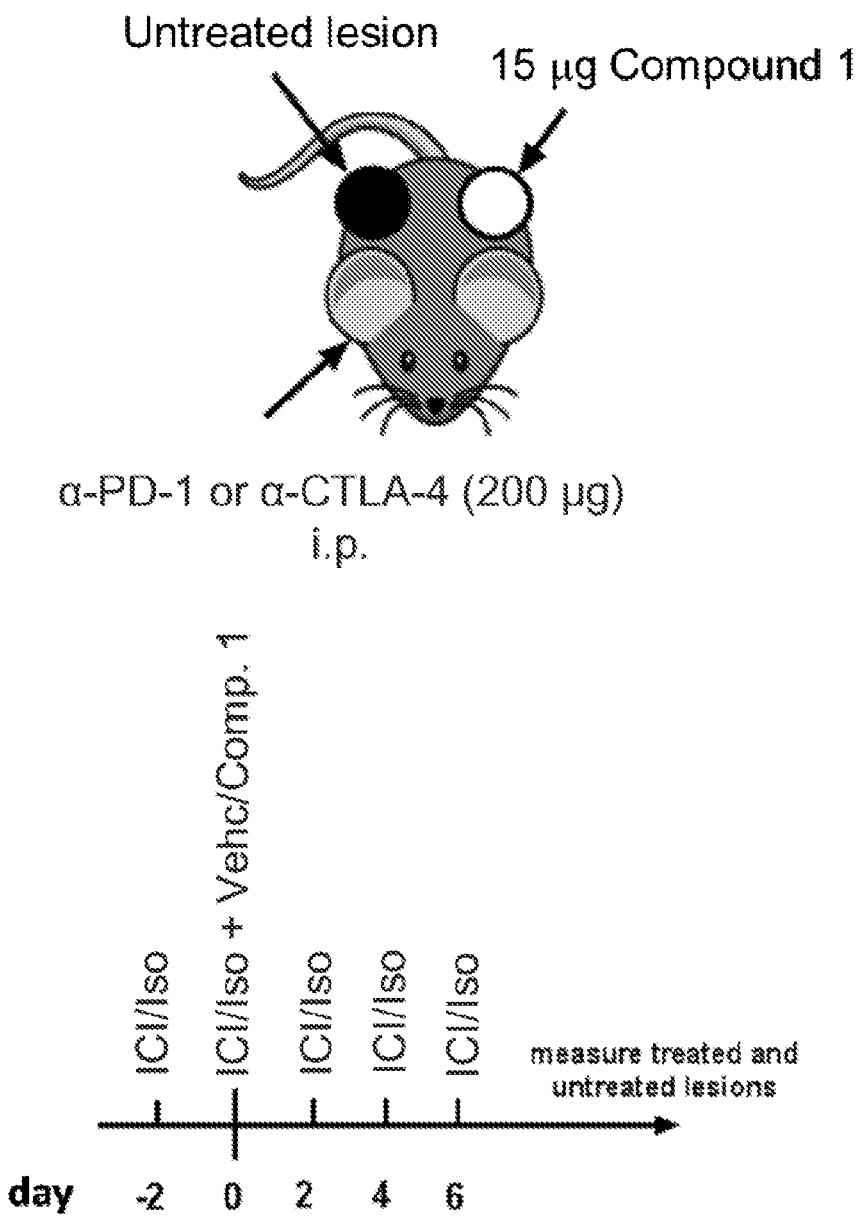
FIG. 7A provides: A schematic diagram of the combination therapy approach: index and bystander tumour are shown together with dosage regime.

Example 7: Observation of Abscopal Effects when Using Compound 1 in Combination with Immune Checkpoint Inhibitors A schematic of the experimental approach can be seen in FIG. 7A. Briefly, 6-7 week old C57BL/6 mice were injected s.c. on both flanks with B16-F10-OVA mouse melanoma cells ($2 \times 10^5$ cells per site in 100 µl). Tumours were allowed to develop to approximately 5-50 mm$^3$, after which 200 µg of anti-PD-1 (RMP1-14, BioXCell), anti-CTLA-4 (9H10, BioXCell) or isotype control antibody (2A3, BioXCell) was injected i.p. per mouse (day −2). On day 0, the largest of the two tumours (approx. 50-75 mm$^3$) was injected I.T. with either Compound 1 (15 µg in 50 µL) or vehicle (Vehc.) only. The remaining tumour was left untreated and each mouse received an additional i.p. injection of the same antibody that was administered on day −2 (again, 200 µg). Antibody was administered for a further 3 times via i.p. injection every 2 days. The volume of both treated and untreated tumours was measured during the course of the experiment as previously detailed.

Figure 7B:
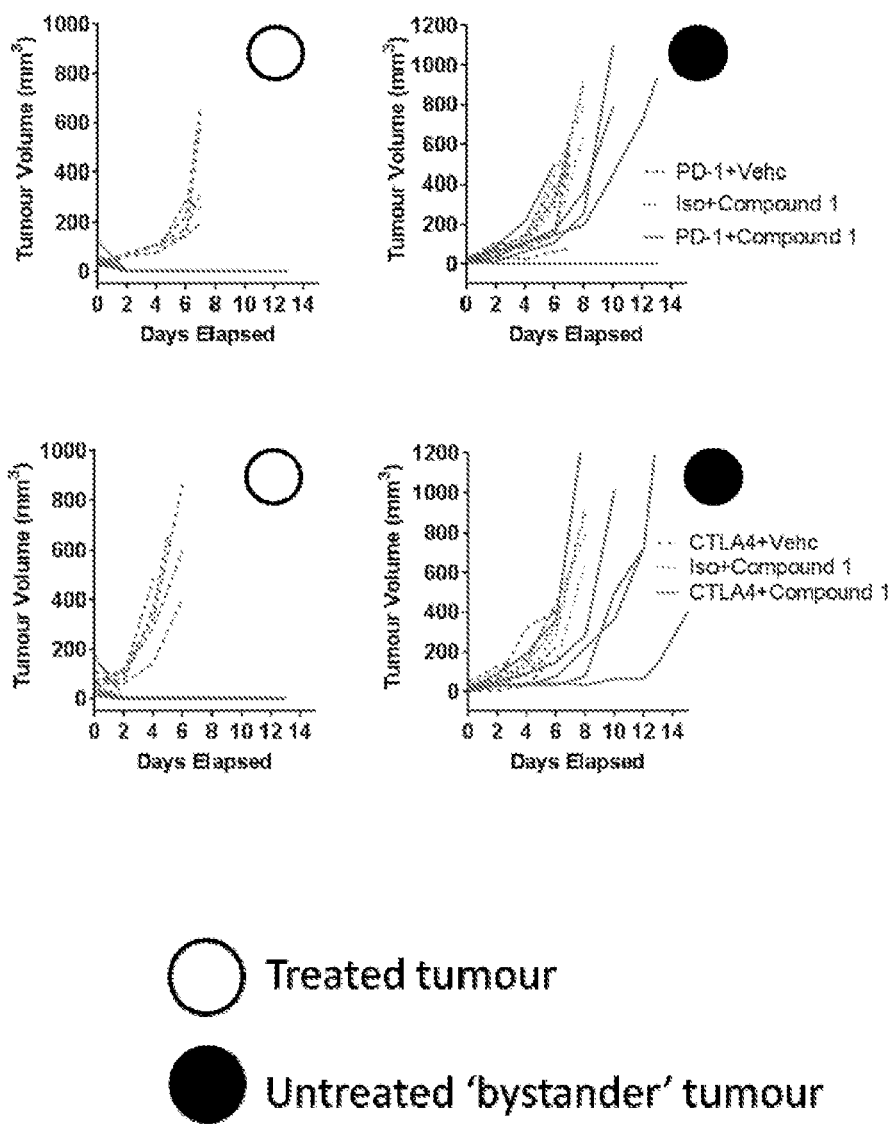
FIG. 7B: Graphical representations of the combination therapy results (tumour volumes). Isotype antibody+Compound 1 (dot line), Anti-PD-1 antibody or Anti-CTLA-4 antibody+vehicle (dash line) and Anti-PD-1 antibody or Anti-CTLA-4 antibody+Compound 1 (solid line) in treated (white circles) and bystander (black circles) tumours.

The results are shown in FIG. 7B. The results show that not only were the tumours treated with a combination of the antibodies and Compound 1 effectively ablated, but that some untreated adjacent tumours also showed a response to the combination therapy that was not observed with either agent alone.

Example 8: Myeloid Derived Suppressor Cells May Affect Low Dose Efficacy of Compound 1

Myeloid derived suppressor cells (MDSCs) are immature myeloid cells that can suppress host immune response to tumours via multiple pathways (Qu et al. 2016). We have used granulocyte colony-stimulating factor (GCSF) knock-out C57BL/6 mice to provide a model for assessing the future potential for possible combination therapies involving Compound 1 with molecules that inhibit or block proteins (e.g. indoleamine 2,3-dioxygenase (IDO)) associated with MDSC recruitment and function. GCSF, an essential regulator of neutrophil production and trafficking, also plays a critical role in migration and proliferation of MDSCs (Li et al. 2016). Using our GCSFR knock-out model the possible role of granulocyte derived MSDCs in limiting the efficacy of monotherapy (at a sub-optimal dose) of Compound 1 against MC38 colorectal adenocarincomas was examined.

Figure 8:
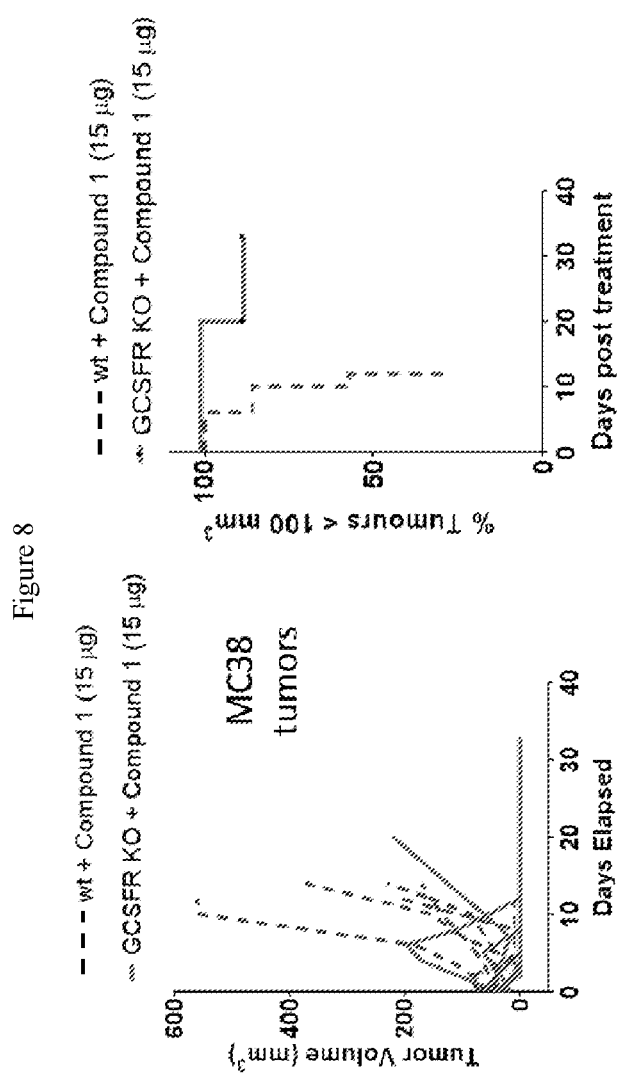
FIG. 8 provides both volume (left panel) and Kaplan-Meier (right panel) based analyses of tumours (% tumours <100 mm$^3$) injected with a sub-optimal dose of Compound 1 (15 µg) in wt and GCSF knockout backgrounds.

Briefly, 6-7 week old wt C57BL/6 and gcsfr$^{-/-}$ mice were injected s.c. on both flanks with MC38 mouse colorectal cancer cells ($1 \times 10^6$ cells per site in 100 µl). Tumours were allowed to develop to approximately 5-50 mm$^3$, after which 15 µg of Compound 1 or vehicle (Vehc.) was injected I.T. (50 µl). The volume of the treated tumours were followed as previously detailed in Examples 6 and 7. Tumour size and survival comparisons between Compound 1 injected tumours in wild type (wt) and GCSFR knockout mice can be seen in FIG. 8.

Given the role of GCSFR in granulocyte recruitment, these data suggest that such immune cell infiltration may be limiting the anti-cancer efficacy of Compound 1 at a known suboptimal dose (15 µg). Combinations of Compound 1 or analogues with compounds that prevent the development of such immunosuppressive cell populations (e.g. IDO inhibitors) may thus lead to better anti-cancer efficacy and improve patient survival.

It will be understood to persons skilled in the art of the invention that many modifications may be made without departing from the spirit and scope of the invention.

REFERENCES

It is to be understood that, if any prior art publication is referred to herein, such reference does not constitute an admission that the publication forms a part of the common general knowledge in the art, in Australia or any other country.

Adams et al. 2015. Big opportunities for small molecules in immuno-oncology. Nature Reviews Drug Discovery 14, 603-622.

Anel et al. 2012. Protein kinase C θ (PKCθ) in natural killer cell function and anti-tumour immunity. Frontiers in Immunology 3, 187.

Beyaert R, & Fiers W. 1994. Molecular mechanisms of tumor necrosis factor-induced cytotoxicity. What we do understand and what we do not. FEBS Letters 340:9-16.

Bos & Sherman. 2010. CD4+ T-cell help in the tumor milieu is required for recruitment and cytolytic function of CD8+ T lymphocytes. Cancer Research 70: 8368-8377.

Boyle et al. 2014. Intralesional injection of the novel PKC activator EBC-46 rapidly ablates tumours in mouse models. PLoS One 9, e108777.

Brezar et al. 2015. PKC-Theta in regulatory and effector T-cell functions. Frontiers in Immunology 6, 530.

Burkholder et al. 2014. Tumor-induced perturbations of cytokines and immune cell networks. BBA-Reviews on Cancer. 1845: 182-201.

Chan et al. 2013. Detection of necrosis by release of lactate dehydrogenase activity. Methods Molecular Biology 979: 65-70.

Cohen et al. 2000. CD4+ T cells in adoptive immunotherapy and the indirect mechanism of tumor rejection. Critical Reviews Immunolology 2: 85-95.

DeNardo et al. 2010. Interactions between lymphocytes and myeloid cells regulate pro-versus anti-tumor immunity. Cancer and Metastasis Reviews 29: 309-316.

Dyer et al. 2016. Oncolytic group B enadenotucirev mediates non-apoptotic cell death with membrane disruption and release of inflammatory mediators. Molecular Therapy Oncolytics. 4: 18-30.

Fridman et al. 2012. The immune contexture in human tumours: impact on clinical outcome. Nature Reviews Cancer 12: 298-306.

Gabrilovic et al. 2012. Coordinated regulation of myeloid cells by tumours. Nature Reviews Immunology 12: 253-268.

Galluzzi et al. 2017. Immunogenic cell death in cancer and infectious disease. Nature Reviews Immunology 17: 97-111.

Garg et al. 2017. Pathogen response-like recruitment and activation of neutrophils by sterile immunogenic dying cells drives neutrophil-mediated residual cell killing. Cell Death Differentiation. Advance online publication 24 Feb. 2017.

Gomez-Cadena et al. 2016. Immune-system-dependent anti-tumour activity of a plant-derived polyphenol rich fraction in a melanoma mouse model. Cell Death and Disease 7: e2243.

Guermonprez et al. 2002. Antigen presentation and T cell stimulation by dendritic cells. Annual Review of Immunology 20: 621-667.

Haabeth et al. 2011. Inflammation driven by tumour-specific Th cells protects against B-cell cancer. Nature Communications 2: 240.

Haabeth et al. 2016. Interleukin-1 is required for cancer eradication mediated by tumor-specific Th1 cells. Oncoimmunology 5 (1): e1039763.

Haabeth OA & Corthnay A. 2012. A model for cancer-suppressive inflammation. Oncoimmunology. 1 (7): 1146-1155.

Hori et al. 1989. Role of tumor necrosis factor and interleukin 1 in gamma-interferon-promoted activation of mouse tumoricidal macrophages. Cancer Research 49:2606-2614.

Hu-Lieskovan et al. 2017. New combination strategies using Programmed Cell Death 1/Programmed Cell Death Ligand 1 checkpoint inhibitors as a backbone. The Cancer Journal 23, 10-22.

Kang et al. 2001. PKCβ modulates antigen receptor signaling via regulation of Btk membrane localisation. EMBO J 20, 5692-5702.

Kim et al. 2003. Mitochondrial permeability transition: a common pathway to necrosis and apoptosis. Biochemical Biophysical Research Communications 304: 463-470.

Knutson K L & Disis M L. 2005. Tumor antigen-specific T helper cells in cancer immunity and immunotherapy. Cancer Immunol Immunother. 54:721-728.

Kolaczkowska E & Kubes P 2013. Neutrophil recruitment and function in health and inflammation. Nature Reviews Immunology 13: 159-175.

Kroemer et al. 2013. Immunogenic cell death in cancer therapy. Annual Reviews Immunology 31: 51-72.

Li et al. 2016. G-CSF is a key modulator of MSC and could be a potential therapeutic target in colitis-associated colorectal cancers. Protein Cell 7: 130-140.

Lim et al. 2015. Protein kinase C in the immune system: from signaling to chromatin regulation. Immunology 146, 508-522.

Mahoney et al. 2015. Combination cancer immunotherapy and new immunomodulatory targets. Nature Reviews Drug Discovery 14, 561-585.

Merad et al. 2013. The Dendritic Cell Lineage: Ontogeny and Function of Dendritic Cells and Their Subsets in the Steady State and the Inflamed Setting. Annual Review of Immunology 31: 563-604.

Msaouel P & Massarelli E 2016. Immune Checkpoint Therapy in Head and Neck Cancers. The Cancer Journal. 22: 108-116.

Neuzillet et al. 2015. Targeting the TGFβ pathway for cancer therapy. Pharmacology & Therapeutics 147: 22-31.

O'Brien et al. 2014. Local ablative therapies: Opportunities for maximising immune engagement and activation. BBA Reviews Cancer 1846: 510-523.

O'Donnell et al. 2017. Resistance to PD1/PDL1 checkpoint inhibition. Cancer Treatment Reviews 52: 71-81.

Pages et al. 2010. Immune infiltration in human tumors: a prognostic factor that should not be ignored. Oncogene, 29: 1093-1102.

Pfeifhofer et al. 2006. PKCa is expressed in T-cells and knockout mice have T-cell activation and immunity defects. Journal of Immunology 176, 6004-6011.

Qu et al. 2016. Expansion and functions of myeloid derived suppressor cells in the tumour microenvironment. Cancer Letters 380: 253-256.

Ribas et al. 2017. Oncolytic Virotherapy Promotes Intratumoral T Cell Infiltration and Improves Anti-PD-1 Immunotherapy. Cell 170(6):1109-19.e10.

Senovilla et al. 2012. Trial watch: prognostic and predictive value of the immune infiltrate in cancer. Oncoimmunology 1: 1323-1343.

Sharma P & Allison JP 2015. The future of immune checkpoint therapy. Science. 348(6230):56-61.

Smyth et al. 2015. Combination cancer immunotherapies tailored to the tumour microenvironment. Nature Reviews Clinical Oncology 13, 143-158.

Sugarman et al. 1985. Recombinant human tumor necrosis factor-alpha: effects on proliferation of normal and transformed cells in vitro. Science 230:943-945.

Workenhe et al. 2014. Immunogenic HSV-mediated oncolysis shapes the antitumor immune response and contributes to therapeutic efficacy. Molecular therapy: the journal of the American Society of Gene Therapy. 22: 123-31.

The claims defining the invention are as follows:

1. A method of treating a tumour comprising administering to a subject in need thereof, an epoxytigliane compound or a pharmaceutically acceptable salt thereof and an immune checkpoint inhibitor; wherein the epoxytigliane compound is administered locally to the tumour;

wherein the epoxytigliane compound is a compound of formula (I):

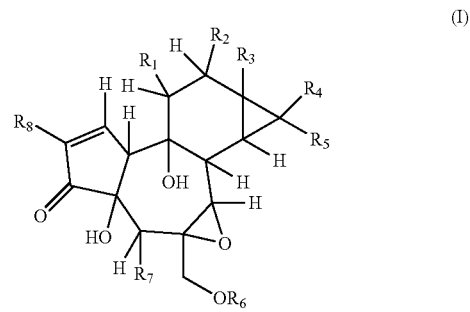

or a geometric isomer or stereoisomer or a pharmaceutically acceptable salt thereof;

wherein $R_1$ is hydrogen or $C_{1-6}$alkyl;

$R_2$ is —OH or —$OR_9$;

$R_3$ is —OH or —$OR_9$;

$R_4$ and $R_5$ are independently selected from hydrogen and $C_{1-6}$alkyl;

$R_6$ is hydrogen or —$R_{10}$;

$R_7$ is hydroxy or $OR_{10}$;

$R_8$ is hydrogen or $C_{1-6}$alkyl;

$R_9$ is —$C_{1-20}$alkyl, —$C_{2-20}$alkenyl, —$C_{2-20}$alkynyl, —C(O)$C_{1-20}$alkyl, —C(O)$C_{2-20}$alkenyl, —C(O)$C_{2-20}$alkynyl, —C(O)cycloalkyl, —C(O)$C_{1-10}$alkylcycloalkyl, —C(O)$C_{2-10}$alkenylcycloalkyl, —C(O)$C_{2-10}$alkynylcycloalkyl, —C(O)aryl, —C(O)$C_{1-10}$alkylaryl, —C(O)$C_{2-10}$alkenylaryl, —C(O)$C_{2-10}$alkynylaryl, —C(O)$C_{1-10}$alkylC(O)$R_{11}$, —C(O)$C_{2-10}$alkenylC(O)$R_{11}$, —C(O)$C_{2-10}$alkynylC(O)$R_{11}$, —C(O)$C_{1-10}$alkylCH($OR_{11}$)($OR_{11}$), —C(O)$C_{2-10}$alkenyl-CH($OR_{11}$)($OR_{11}$), —C(O)$C_{2-10}$alkynylCH($OR_{11}$)($OR_{11}$), —C(O)$C_{1-10}$alkylS$R_{11}$, —C(O)$C_{2-10}$alkenylS$R_{11}$, —C(O)$C_{2-10}$alkynylS$R_{11}$, —C(O)$C_{1-10}$alkylC(O)$OR_{11}$, —C(O)$C_{2-10}$alkenylC(O)$OR_{11}$, —C(O)$C_{2-10}$alkynylC(O)$OR_{11}$, —C(O)

$C_{1-10}$alkyl-C(O)SR$_{11}$, —C(O)C$_{2-10}$alkenylC(O)SR$_{11}$, —C(O)C$_{2-10}$alkynylC(O)SR$_{11}$,

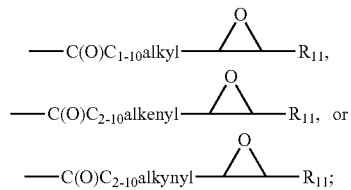

$R_{10}$ is —C$_{1-6}$alkyl, —C$_{2-6}$alkenyl, —C$_{2-6}$alkynyl, —C(O)C$_{1-6}$alkyl, —C(O)C$_{2-6}$alkenyl, —C(O)C$_{2-6}$alkynyl, —C(O)aryl, —C(O)C$_{1-6}$alkylaryl, —C(O)C$_{2-6}$alkenylaryl, or —C(O)C$_{2-6}$alkynylaryl; and $R_{11}$ is hydrogen, —C$_{1-10}$alkyl, —C$_{2-10}$alkenyl, —C$_{2-10}$alkynyl, cycloalkyl or aryl;

wherein each alkyl, alkenyl, alkynyl, cycloalkyl or aryl group is optionally substituted with one or more optional substituents selected from the group consisting of C$_{1-6}$alkyl, C$_{2-6}$alkenyl, C$_{3-6}$cycloalkyl, oxo (=O), —OH, —SH, C$_{1-6}$alkylO-, C$_{2-6}$alkenylO-, C$_{3-6}$cycloalkylO-, C$_{1-6}$alkylS-, C$_{2-6}$alkenylS-, C$_{3-6}$cycloalkylS-, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —CN, —NO$_2$, -halogen, —CF$_3$, —OCF$_3$, —SCF$_3$, —CHF$_2$, —OCHF$_2$, —SCHF$_2$, -phenyl, —C$_{1-6}$alkylphenyl, —Ophenyl, —C(O)phenyl, and —C(O)C$_{1-6}$alkyl;

wherein the immune checkpoint inhibitor is selected from an antagonist of Programmed Death 1 (PD-1) receptor or its ligand PD-L1, and an antagonist of Cytotoxic T-Lymphocyte-Associated protein 4 (CTLA-4); and wherein the tumour is one that has acquired or has intrinsic resistance to monotherapy with the immune checkpoint inhibitor.

2. A method of treating one or more bystander tumours in a subject comprising administering to a subject in need thereof, an epoxytigliane compound or a pharmaceutically acceptable salt thereof and an immune checkpoint inhibitor; wherein the epoxytigliane compound is administered locally to a tumour other than the one or more bystander tumours;

wherein the epoxytigliane compound is a compound of formula (I):

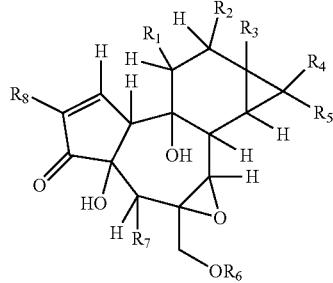

(I)

or a geometric isomer or stereoisomer or a pharmaceutically acceptable salt thereof;

wherein $R_1$ is hydrogen or C$_{1-6}$alkyl;

$R_2$ is —OH or —OR$_9$;

$R_3$ is —OH or —OR$_9$;

$R_4$ and $R_5$ are independently selected from hydrogen and C$_{1-6}$alkyl;

$R_6$ is hydrogen or —R$_{10}$;

$R_7$ is hydroxy or OR$_{10}$;

$R_8$ is hydrogen or C$_{1-6}$alkyl;

$R_9$ is —C$_{1-20}$alkyl, —C$_{2-20}$alkenyl, —C$_{2-20}$alkynyl, —C(O)C$_{1-20}$alkyl, —C(O)C$_{2-20}$alkenyl, —C(O)C$_{2-20}$alkynyl, —C(O)cycloalkyl, —C(O)C$_{1-10}$alkylcycloalkyl; —C(O)C$_{2-10}$alkenylcycloalkyl, —C(O)C$_{2-10}$alkynylcycloalkyl, —C(O)aryl, —C(O)C$_{1-10}$alkylaryl, —C(O)C$_{2-10}$alkenylaryl, —C(O)C$_{2-10}$alkynylaryl, —C(O)C$_{1-10}$alkylC(O)R$_{11}$, —C(O)C$_{2-10}$alkenylC(O)R$_{11}$, —C(O)C$_{2-10}$alkynylC(O)R$_{11}$, —C(O)C$_{1-10}$alkylCH(OR$_{11}$)(OR$_{11}$), —C(O)C$_{2-10}$alkenyl-CH(OR$_{11}$)(OR$_{11}$), —C(O)C$_{2-10}$alkynylCH(OR$_{11}$)(OR$_{11}$), —C(O)C$_{1-10}$alkylSR$_{11}$, —C(O)C$_{2-10}$alkenylSR$_{11}$, —C(O)C$_{2-10}$alkynylSR$_{11}$, —C(O)C$_{1-10}$alkylC(O)OR$_{11}$, —C(O)C$_{2-10}$alkenylC(O)OR$_{11}$, —C(O)C$_{2-10}$alkynylC(O)OR$_{11}$, —C(O)C$_{1-10}$alkyl-C(O)SR$_{11}$, —C(O)C$_{2-10}$alkenylC(O)SR$_{11}$, —C(O)C$_{2-10}$alkynylC(O)SR$_{11}$,

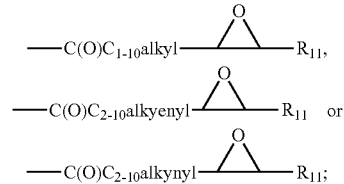

$R_{10}$ is —C$_{1-6}$alkyl, —C$_{2-6}$alkenyl, —C$_{2-6}$alkynyl, —C(O)C$_{1-6}$alkyl, —C(O)C$_{2-6}$alkenyl, —C(O)C$_{2-6}$alkynyl, —C(O)aryl, —C(O)C$_{1-6}$alkylaryl, —C(O)C$_{2-6}$alkenylaryl, or —C(O)C$_{2-6}$alkynylaryl; and $R_{11}$ is hydrogen, —C$_{1-10}$alkyl, —C$_{2-10}$alkenyl, —C$_{2-10}$alkynyl, cycloalkyl or aryl;

wherein each alkyl, alkenyl, alkynyl, cycloalkyl or aryl group is optionally substituted with one or more optional substituents selected from the group consisting of C$_{1-6}$alkyl, C$_{2-6}$alkenyl, C$_{3-6}$cycloalkyl, oxo (=O), —OH, —SH, C$_{1-6}$alkylO-, C$_{2-6}$alkenylO-, C$_{3-6}$cycloalkylO-, C$_{1-6}$alkylS-, C$_{2-6}$alkenylS-, C$_{3-6}$cycloalkylS-, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —CN, —NO$_2$, -halogen, —CF$_3$, —OCF$_3$, —SCF$_3$, —CHF$_2$, —OCHF$_2$, —SCHF$_2$, -phenyl, —C$_{1-6}$alkylphenyl, —Ophenyl, —C(O)phenyl, and —C(O)C$_{1-6}$alkyl;

wherein the immune checkpoint inhibitor is selected from an antagonist of Programmed Death 1 (PD-1) receptor or its ligand PD-L1, or an antagonist of Cytotoxic T-Lymphocyte-Associated protein 4 (CTLA-4), and wherein the tumour to which the epoxytigliane is administered is one that has acquired or has intrinsic resistance to monotherapy with the immune checkpoint inhibitor.

3. The method according to claim 1 wherein the epoxytigliane compound is administered by intra-tumoural injection.

4. The method according to claim 1 wherein the immune checkpoint inhibitor is administered systemically.

5. The method according to claim 4 wherein the immune checkpoint inhibitor is administered by parenteral injection.

6. The method according to claim 1 wherein $R_1$ is —$CH_3$.

7. The method according to claim 1 wherein $R_2$ and $R_3$ are independently selected from —OC(O)$C_{1-20}$alkyl, —OC(O)$C_{2-20}$alkenyl, —OC(O)$C_{2-20}$alkynyl, —OC(O)cycloalkyl, —OC(O)$C_{1-10}$alkylcycloalkyl; —OC(O)$C_{2-10}$alkenylcycloalkyl, —OC(O)$C_{2-10}$alkynylcycloalkyl, —OC(O)aryl, —OC(O)$C_{1-10}$alkylaryl, —OC(O)$C_{2-10}$alkenylaryl, —OC(O)$C_{2-10}$alkynylaryl, —OC(O)$C_{1-10}$alkylC(O)$R_{11}$, —OC(O)$C_{2-10}$alkenylC(O)$R_{11}$, —OC(O)$C_{2-10}$alkynylC(O)$R_{11}$, —OC(O)$C_{1-10}$alkylCH(O$R_{11}$)(O$R_{11}$), —OC(O)$C_{2-10}$alkenylCH(O$R_{11}$)(O$R_{11}$), —OC(O)$C_{2-10}$alkynylCH(O$R_{11}$)(O$R_{11}$), —OC(O)$C_{1-10}$alkylS$R_{11}$, —OC(O)$C_{2-10}$alkenylS$R_{11}$, —OC(O)$C_{2-10}$alkynylS$R_{11}$, —OC(O)$C_{1-10}$alkylC(O)O$R_{11}$, —OC(O)$C_{2-10}$alkenylC(O)O$R_{11}$, —OC(O)$C_{2-10}$alkynylC(O)O$R_{11}$, —OC(O)$C_{1-10}$alkylC(O)S$R_{11}$, —OC(O)$C_{2-10}$alkenylC(O)S$R_{11}$ and —OC(O)$C_{2-10}$alkynylC(O)S$R_{11}$.

8. The method according to claim 1 wherein $R_4$ and $R_5$ are each independently selected from H and —$CH_3$.

9. The method according to claim 1 wherein $R_6$ is hydrogen, —C(O)$C_{1-6}$alkyl, —C(O)$C_{2-6}$alkenyl, —C(O)$C_{2-6}$alkynyl or —C(O)aryl.

10. The method according to claim 1 wherein $R_7$ is hydroxyl, —OC(O)$C_{1-6}$alkyl, —OC(O)$C_{2-6}$alkenyl or —OC(O)$C_{2-6}$alkynyl.

11. The method according to claim 1 wherein $R_5$ is H or —$CH_3$.

12. The method according to claim 1 wherein the epoxytigliane compound of formula (I) is selected from the following compounds:
12-tigloyl-13-(2-methylbutanoyl)-6,7-epoxy-4,5,9,12,13,20-hexahydroxy-1-tiglien-3-one;
12,13-di-(2-methylbutanoyl)-6,7-epoxy-4,5,9,12,13,20-hexahydroxy-1-tiglien-3-one;
12-hexanoyl-13-(2-methylbutanoyl)-6,7-epoxy-4,5,9,12,13,20-hexahydroxy-1-tiglien-3-one;
12,13-dihexanoyl-6,7-epoxy-4,5,9,12,13,20-hexahydroxy-1-tiglien-3-one;
12-myristoyl-13-(2-methylbutanoyl)-6,7-epoxy-4,5,9,12,13,20-hexahydroxy-1-tiglien-3-one;
12-tigloyl-13-(2-methylbutanoyl)-6,7-epoxy-4,5,9,12,13-pentahydroxy-20-acetyloxy-1-tiglien-3-one;
12-myristoyl-13-acetyloxy-6,7-epoxy-4,5,9,12,13,20-hexahydroxy-1-tiglien-3-one;
12-propanoyl-13-2-methylbutanoyl)-6,7-epoxy-4,5,9,12,13,20-hexahydroxy-1-tiglien-3-one; 12,13-ditigloyl-6,7-epoxy-4,5,9,12,13,20-hexahydroxy-1-tiglien-3-one; and
12-(2-methylbutanoyl)-13-tigloyl-6,7-epoxy-4,5,9,12,13,20-hexahydroxy-1-tiglien-3-one;
or a pharmaceutically acceptable salt thereof.

13. The method according to claim 1 wherein the immune checkpoint inhibitor is an antagonist of Programmed Death 1 (PD-1) receptor or Cytotoxic T-Lymphocyte-Associated protein 4 (CTLA-4).

14. The method according to claim 1 wherein the immune checkpoint inhibitor is administered in multiple doses.

15. The method according to claim 14 wherein the multiple doses are administered prior to, simultaneously with and/or subsequent to the administration of the epoxytigliane compound.

16. A pharmaceutical composition comprising an epoxytigliane compound or a pharmaceutically acceptable salt thereof and an immune checkpoint inhibitor and optionally a pharmaceutically acceptable carrier; wherein the epoxytigliane compound is a compound of formula (I):

or a geometric isomer or stereoisomer or a pharmaceutically acceptable salt thereof,
wherein
$R_1$ is hydrogen or $C_{1-6}$alkyl,
$R_2$ is —OH or —O$R_9$;
$R_3$ is —OH or —O$R_9$;
$R_4$ and $R_5$ are independently selected from hydrogen and $C_{1-6}$alkyl,
$R_6$ is hydrogen or -$R_{10}$;
$R_7$ is hydroxy or O$R_{10}$;
$R_8$ is hydrogen or $C_{1-6}$alkyl;
$R_9$ is —$C_{1-20}$alkyl, —$C_{2-20}$alkenyl, —$C_{2-20}$alkynyl, —C(O)$C_{1-20}$alkyl, —C(O)$C_{2-20}$alkenyl, —C(O)$C_{2-20}$alkynyl, —C(O)cycloalkyl, —C(O)$C_{1-10}$alkylcycloalkyl, —C(O)$C_{2-10}$alkenylcycloalkyl, —C(O)$C_{2-10}$alkynylcycloalkyl, —C(O)aryl, —C(O)$C_{1-10}$alkylaryl, —C(O)$C_{2-10}$alkenylaryl, —C(O)$C_{2-10}$alkynylaryl, —C(O)$C_{1-10}$alkylC(O)$R_{11}$, —C(O)$C_{2-10}$alkenylC(O)$R_{11}$, —C(O)$C_{2-10}$alkynylC(O)$R_{11}$, —C(O)$C_{1-10}$alkylCH(O$R_{11}$)(O$R_{11}$), —C(O)$C_{2-10}$alkenylCH(O$R_{11}$)(O$R_{11}$), —C(O)$C_{2-10}$alkynylCH(O$R_{11}$)(O$R_{11}$), —C(O)$C_{1-10}$alkylS$R_{11}$, —C(O)$C_{2-10}$alkenylS$R_{11}$, —C(O)$C_{2-10}$alkynylS$R_{11}$, —C(O)$C_{1-10}$alkylC(O)O$R_{11}$, —C(O)$C_{2-10}$alkenylC(O)O$R_{11}$, —C(O)$C_{2-10}$alkynylC(O)O$R_{11}$, —C(O)$C_{1-10}$alkyl-C(O)S$R_{11}$, —C(O)$C_{2-10}$alkenylC(O)S$R_{11}$, —C(O)$C_{2-10}$alkynylC(O) S$R_{11}$, —C(O)$C_{1-10}$alkyl——△——$R_{11}$, —C(O)$C_{2-10}$alkyenyl——△——$R_{11}$ or —C(O)$C_{2-10}$alkynyl——△——$R_{11}$;

$R_{10}$ is —$C_{1-6}$alkyl, —$C_{2-6}$alkenyl, —$C_{2-6}$alkynyl, —C(O)$C^{1-6}$alkyl, —C(O)$C_{2-6}$alkenyl, —C(O)$C_{2-6}$alkynyl, —C(O)aryl, —C(O)$C_{1-6}$alkylaryl, —C(O)$C_{2-6}$alkenylaryl, or —C(O)$C_{2-6}$alkynylaryl, and $R_{11}$ is hydrogen, —$C_{1-10}$alkyl, cycloalkyl or aryl;
wherein each alkyl, alkenyl, alkynyl, cycloalkyl or aryl group is optionally substituted with one or more optional substituents selected from the group consisting of $C_{1-6}$alkyl, $C_{2-6}$alkenyl, $C_{3-6}$cycloalkyl, oxo (=O), —OH, —SH, $C_{1-6}$alkylO-, $C_{2-6}$alkenylO-, $C_{3-6}$cycloalkylO-, $C_{1-6}$alkylS-, $C_{2-6}$alkenylS-, $C_{3-6}$cycloalkylS-, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —CN, —NO$_2$, -halogen, —CF$_3$, —OCF$_3$, —SCF$_3$, —CHF$_2$, —OCHF$_2$, —SCHF$_2$—, -phenyl, —C$_{1-6}$alkylphenyl, —Ophenyl, —C(O)phenyl, and —C(O)C$_{1-6}$alkyl; and wherein the immune checkpoint inhibitor is selected from an antagonist of Programmed Death 1 (PD-1) receptor or its ligand PD-L1, or an antagonist of Cytotoxic T-Lymphocyte-Associated protein 4 (CTLA-4).

17. The kit comprising one or more doses of epoxytigliane compound and one or more doses of immune checkpoint inhibitor; wherein the epoxytigliane compound is a compound of formula (I):

(I)

or a geometric isomer or stereoisomer or a pharmaceutically acceptable salt thereof;
wherein
$R_1$ is hydrogen or $C_{1-6}$alkyl;
$R_2$ is —OH or —OR$_9$;
$R_3$ is —OH or —OR$_9$;
$R_4$ and $R_5$ are independently selected from hydrogen and $C_{1-6}$alkyl;
$R_6$ is hydrogen or -$R_{10}$;
$R_7$ is hydroxy or OR$_{10}$;
$R_8$ is hydrogen or $C_{1-6}$alkyl;
$R_9$ is —$C_{1-20}$alkyl, —$C_{2-20}$alkenyl, —$C_{2-20}$alkynyl, —C(O)C$_{1-20}$alkyl, —C(O)C$_{2-20}$alkenyl, —C(O)C$_{2-20}$alkynyl, —C(O)cycloalkyl, —C(O)C$_{1-10}$alkylcycloalkyl; —C(O)C$_{2-10}$alkenyl-cycloalkyl, —C(O)C$_{2-10}$alkynylcycloalkyl, —C(O)aryl, —C(O)C$_{1-10}$alkylaryl, —C(O)C$_{2-10}$alkenylaryl, —C(O)C$_{2-10}$alkynylaryl, —C(O)C$_{1-10}$alkylC(O)R$_{11}$, —C(O)C$_{2-10}$alkenylC(O)R$_{11}$, —C(O)C$_{2-10}$alkynylC(O)R$_{11}$, —C(O)C$_{1-10}$alkylCH(OR$_{11}$)(OR$_{11}$), —C(O)C$_{2-10}$alkenylCH(OR$_{11}$)(OR$_{11}$), —C(O)C$_{2-10}$alkynylCH(OR$_{11}$)(OR$_{11}$), —C(O)C$_{1-10}$alkylSR$_{11}$, —C(O)C$_{2-10}$alkenylSR$_{11}$, —C(O)C$_{2-10}$alkynylSR$_{11}$, —C(O)C$_{1-10}$alkylC(O)OR$_{11}$, —C(O)C$_{2-10}$alkenylC(O)OR$_{11}$, —C(O)C$_{2-10}$alkynylC(O)OR$_{11}$, —C(O)C$_{1-10}$alkyl-C(O)SR$_{11}$, —C(O)C$_{2-10}$alkenylC(O)SR$_{11}$, —C(O)C$_{2-10}$alkynylC(O)SR$_{11}$, $R_{10}$ is —$C_{1-6}$alkyl, —$C_{2-6}$alkenyl, —$C_{2-6}$alkynyl, —C(O)C$_{1-6}$alkyl, —C(O)C$_{2-6}$alkenyl, —C(O)C$_{2-6}$alkynyl, —C(O)aryl, —C(O)C$_{1-6}$alkylaryl, —C(O)C$_{2-6}$alkenylaryl, or —C(O)C$_{2-6}$alkynylaryl; and $R_{11}$ is hydrogen, —$C_{1-10}$alkyl, —$C_{2-10}$alkenyl, —$C_{2-10}$alkynyl, cycloalkyl or aryl;

wherein each alkyl, alkenyl, alkynyl, cycloalkyl or aryl group is optionally substituted with one or more optional substituents selected from the group consisting of $C_{1-6}$alkyl, $C_{2-6}$alkenyl, $C_{3-6}$cycloalkyl, oxo (=O), —OH, —SH, $C_{1-6}$alkylO-, $C_{2-6}$alkenylO-, $C_{3-6}$cycloalkylO-, $C_{1-6}$alkylS-, $C_{2-6}$alkenylS-, $C_{3-6}$cycloalkylS-, —CO$_2$H, —CO$_2$C$_{1-6}$alkyl, —NH$_2$, —NH(C$_{1-6}$alkyl), —N(C$_{1-6}$alkyl), —NH(phenyl), —N(phenyl)$_2$, —CN, —NO, -halogen, —CF, —OCHF$_2$, —SCHF$_2$, -phenyl, —C$_{1-6}$alkylphenyl, —Ophenyl, —C(O)phenyl, and —C(O)C$_{1-6}$alkyl; and wherein the immune checkpoint inhibitor is selected from an antagonist of Programmed Death 1 (PD-1) receptor or its ligand PD-L1, or an antagonist of Cytotoxic T-Lymphocyte-Associated protein 4 (CTLA-4).

18. The kit according to claim 17 comprising one or more doses of epoxytigliane compound formulated for topical administration and one or more doses of immune checkpoint inhibitor formulated for administration by injection.

19. The kit according to claim 17 comprising one dose of epoxytigliane compound formulated for intra-tumoural injection and one or more doses of immune checkpoint inhibitor formulated for administration by injection.

20. The method according to claim 2 wherein the epoxytigliane compound is administered by intra-tumoural injection.

21. The method according to claim 2 wherein the immune checkpoint inhibitor is administered systemically.

22. The method according to claim 21 wherein the immune checkpoint inhibitor is administered by parenteral injection.

23. The method according to claim 2 wherein one or more of the following applies:
i) $R_1$ is —CH$_3$;
ii) $R_2$ and $R_3$ are independently selected from —OC(O)C$_{1-20}$alkyl, —OC(O)C$_{2-20}$alkenyl, —OC(O)C$_{2-20}$alkynyl, —OC(O)cycloalkyl, —OC(O)C$_{1-10}$alkylcycloalkyl; —OC(O)C$_{2-10}$ alkenylcycloalkyl, —OC(O)C$_{2-10}$alkynylcycloalkyl, —OC(O)aryl, —OC(O)C$_{1-10}$alkylaryl, —OC(O)C$_{2-10}$alkenylaryl, —OC(O)C$_{2-10}$alkynylaryl, —OC(O)C$_{1-10}$alkylC(O)R$_{11}$, —OC(O)C$_{2-10}$alkenylC(O)R$_{11}$, —OC(O)C$_{2-10}$alkynylC(O)R$_{11}$, —OC(O)C$_{1-10}$alkylCH(OR$_{11}$)(OR$_{11}$), —OC(O)C$_{2-10}$alkenylCH(OR$_{11}$)(OR$_{11}$), —OC(O)C$_{2-10}$alkynylCH(OR$_{11}$)(OR$_{11}$), —OC(O)C$_{1-10}$alkylSR$_{11}$, —OC(O)C$_{2-10}$alkenylSR$_{11}$, —OC(O)C$_{2-10}$alkynylSR$_{11}$, —OC(O)C$_{1-10}$alkylC(O)OR$_{11}$, —OC(O)C$_{2-10}$alkenylC(O)OR$_{11}$, —OC(O) C$_{2-10}$alkynylC(O)OR$_{11}$, —OC(O)C$_{1-10}$alkylC(O)SR$_{11}$, —OC(O)C$_{2-10}$alkenylC(O)SR$_{11}$ and —OC(O)C$_{2-10}$alkynylC(O)SR$_{11}$;
iii) $R_4$ and $R_5$ are each independently selected from H and —CH$_3$;
iv) $R_6$ is hydrogen, —C(O)C$_{1-6}$alkyl, —C(O)C$_{2-6}$alkenyl, —C(O)C$_{2-6}$alkynyl or —C(O)aryl;
v) $R_7$ is hydroxyl, —OC(O)C$_{1-6}$alkyl, —OC(O)C$_{2-6}$alkenyl or —OC(O)C$_{2-6}$alkynyl; and
vi) $R_8$ is H or —CH$_3$.

24. The method according to claim 2 wherein the epoxytigliane compound of formula (I) is selected from the following compounds:
- 12-tigloyl-13-(2-methylbutanoyl)-6,7-epoxy-4,5,9,12,13,20-hexahydroxy-1-tiglien-3-one;
- 12,13-di-(2-methylbutanoyl)-6,7-epoxy-4,5,9,12,13,20-hexahydroxy-1-tiglien-3-one;
- 12-hexanoyl-13-(2-methylbutanoyl)-6,7-epoxy-4,5,9,12,13,20-hexahydroxy-1-tiglien-3-one;
- 12,13-dihexanoyl-6,7-epoxy-4,5,9,12,13,20-hexahydroxy-1-tiglien-3-one;
- 12-myristoyl-13-(2-methylbutanoyl)-6,7-epoxy-4,5,9,12,13,20-hexahydroxy-1-tiglien-3-one;
- 12-tigloyl-13-(2-methylbutanoyl)-6,7-epoxy-4,5,9,12,13-pentahydroxy-20-acetyloxy-1-tiglien-3-one;
- 12-myristoyl-13-acetyloxy-6,7-epoxy-4,5,9,12,13,20-hexahydroxy-1-tiglien-3-one;
- 12-propanoyl-13-2-methylbutanoyl)-6,7-epoxy-4,5,9,12,13,20-hexahydroxy-1-tiglien-3-one; 12,13-ditigloyl-6,7-epoxy-4,5,9,12,13,20-hexahydroxy-1-tiglien-3-one; and
- 12-(2-methylbutanoyl)-13-tigloyl-6,7-epoxy-4,5,9,12,13,20-hexahydroxy-1-tiglien-3-one;

or a pharmaceutically acceptable salt thereof.

25. The method according to claim 2 wherein the immune checkpoint inhibitor is an antagonist of Programmed Death 1 (PD-1) receptor or Cytotoxic T-Lymphocyte-Associated protein 4 (CTLA-4).

26. The method according to claim 25 wherein the immune checkpoint inhibitor is selected from an anti-PD-1 antibody and an anti-CTLA4 antibody.

27. The method according to claim 2 wherein the immune checkpoint inhibitor is administered in multiple doses.

28. The method according to claim 27 wherein the multiple doses are administered prior to, simultaneously with and/or subsequent to the administration of the epoxytigliane compound.

29. The method according to claim 13 wherein the immune checkpoint inhibitor is selected from an anti-PD-1 antibody and an anti-CTLA4 antibody.

* * * * *

UNITED STATES PATENT AND TRADEMARK OFFICE
CERTIFICATE OF CORRECTION

PATENT NO. : 11,213,506 B2
APPLICATION NO. : 16/496333
DATED : January 4, 2022
INVENTOR(S) : Paul Warren Reddell et al.

Page 1 of 1

It is certified that error appears in the above-identified patent and that said Letters Patent is hereby corrected as shown below:

In the Claims

Column 30, Claim 2, Line 9:
"$R_5$ is hydrogen" should read: -- $R_8$ is hydrogen --.

Column 31, Claim 11, Line 30:
"$R_5$ is" should read: -- $R_8$ is --.

Column 32, Claim 16, Line 59:
"-C(O)C$^{1-6}$alkyl,-" should read: -- -C(O)C$_{1-6}$alkyl,- --.

Column 32, Claim 16, Line 62:
"-C$_{1-10}$alkyl, cycloalkyl or aryl;" should read: -- -C$_{1-10}$alkyl, -C$_{2-10}$alkenyl, -C$_{2-10}$alkynyl, cycloalkyl or aryl; --.

Column 33, Claim 17, Line 40:
"$R_5$" should read: -- $R_8$ --.

Column 33, Claim 17, Line 55:
"-C(O)C$_{1-10}$alkyl-C(O) SR$_{11}$," should read: -- -C(O)C$_{1-10}$alkyl-C(O)SR$_{11}$, --.

Column 34, Claim 17, Line 17:
"CF, -OCHF$_2$," should read: -- CF$_3$, -OCF$_3$, -SCF$_3$, -CHF$_2$, -OCHF$_2$, --.

Column 34, Claim 23, Line 67:
"$R_5$" should read: -- $R_8$ --.

Signed and Sealed this
Twentieth Day of June, 2023

Katherine Kelly Vidal
*Director of the United States Patent and Trademark Office*